(12) United States Patent
Kudo et al.

(10) Patent No.: US 8,235,958 B2
(45) Date of Patent: Aug. 7, 2012

(54) ABSORBENT ARTICLE AND METHOD FOR PRODUCING ABSORBENT ARTICLE

(75) Inventors: Jun Kudo, Ehime (JP); Hideyuki Kinoshita, Kagawa (JP); Akira Hashino, Kagawa (JP)

(73) Assignee: Uni-Charm Corporation, Ehime (JP)

( * ) Notice: Subject to any disclaimer, the term of this patent is extended or adjusted under 35 U.S.C. 154(b) by 291 days.

(21) Appl. No.: 12/444,618

(22) PCT Filed: Nov. 6, 2007

(86) PCT No.: PCT/JP2007/071543
§ 371 (c)(1),
(2), (4) Date: May 18, 2009

(87) PCT Pub. No.: WO2008/056658
PCT Pub. Date: May 15, 2008

(65) Prior Publication Data
US 2010/0036354 A1 Feb. 11, 2010

(30) Foreign Application Priority Data
Nov. 7, 2006 (JP) ................................. 2006-301744

(51) Int. Cl.
*A61F 13/15* (2006.01)
(52) U.S. Cl. ....... 604/385.11; 604/385.14; 604/385.101; 604/379; 604/380
(58) Field of Classification Search ............. 604/385.11, 604/385.14, 385.101, 379, 380
See application file for complete search history.

(56) References Cited

U.S. PATENT DOCUMENTS

2008/0015538 A1* 1/2008 Deerin ....................... 604/402

FOREIGN PATENT DOCUMENTS

| JP | 53097540 | | 8/1978 |
| JP | 62-56025 | U | 4/1987 |
| JP | 10-286278 | A | 10/1998 |
| JP | 11-104169 | A | 4/1999 |
| JP | 2002-159534 | A | 6/2002 |

OTHER PUBLICATIONS

International Search Report of Application No. PCT/JP2007/071546 mailed Nov. 27, 2007.
Chinese Office Action for Application No. 200780041423.6 mailed Dec. 22, 2011.

* cited by examiner

*Primary Examiner* — Jacqueline F. Stephens
(74) *Attorney, Agent, or Firm* — Lowe, Hauptman, Ham & Berner, LLP

(57) ABSTRACT

The invention provides an absorbent article that is small and that can be easily worn by a user and a method for producing the absorbent article.

The absorbent article that is used in abutment against a user's body includes: an absorbent body for absorbing fluid; and an absorbent-article main body whose face on a side close to the user's body in use is joined to the absorbent body. The absorbent body has a longitudinal direction, a width direction, and a thickness direction. One end section of the absorbent body in the longitudinal direction is undetachably joined to the absorbent-article main body, and another end section of the absorbent body in the longitudinal direction is detachably joined to a portion inside an outer edge of the absorbent-article main body. The absorbent body has a non-joined section that is not joined to the absorbent-article main body, between the joined section on a side close to the other end section and the outer edge of the absorbent-article main body.

10 Claims, 19 Drawing Sheets

ABSORBENT ARTICLE AND METHOD FOR PRODUCING ABSORBENT ARTICLE

RELATED APPLICATIONS

The present application is based on International Application Number PCT/JP2007/071543 filed Nov. 6, 2007, and claims priority from Japanese Application Number 2006-301744, filed Nov. 7, 2006, the disclosures of which are hereby incorporated by reference herein in their entirety.

TECHNICAL FIELD

The present invention relates to an absorbent article and a method for producing the absorbent article.

BACKGROUND ART

Conventionally, as an absorbent article for absorbing a certain fluid such as menstrual blood, an absorbent article is known that includes a main body section absorbing fluid and a surface structure partially fixed to a surface of the main body section, and in which a back face of the main body section includes a fluid-impermeable sheet made of polyethylene or the like in order to prevent leakage of the fluid (see JP-A-2003-79662, for example). Recently, for the purpose of preventing displacement, an absorbent article has been devised including a surface structure that is positioned in use in the front-and-rear direction of user's body, and that has a front side fixed to a main body section and a rear side separable from the main body section, in which the absorbent article is worn such that the rear side of the surface structure is placed in a groove between the buttocks. In addition, an absorbent article has been devised having a structure in which a user pulls up in use the rear end of the surface structure backward, thereby positioning the surface structure in the groove between the buttocks. Herein, when merely the front portion of the surface structure is fixed, a position of the rear end of the surface structure is unstable, and catching the rear end of the surface structure is difficult for the user. Thus, it is desirable that the rear end is temporarily fixed to the main body section in a detachable manner until the absorbent article is used.

DISCLOSURE OF INVENTION

Problem to be Solved by the Invention

When using this sort of conventional absorbent article, a user has to hold the rear end of the surface structure in order to pull up the rear end of the surface structure. If the rear end of the surface structure is temporarily fixed to the main body section, the temporary fixation has to be released, and thus the rear end has to be surely held. Projecting the rear end of the surface structure from the main body section makes the surface structure to be temporarily fixed to the main body section at a position where the surface structure is overlapped with the rear end of the main body section, so that the projected section can be easily held. However, when the rear end of the surface structure is projected extending from the main body section, the total length of the absorbent article increases, the size increases even in a wrapped state, and thus portability may be impaired.

The invention has been made in view of conventional problems as described above, and an advantage thereof is to provide an absorbent article that is small and that can be easily worn by a user, and a method for producing the absorbent article.

Means for Solving the Problem

In order to solve the above-described problem, a primary aspect of the invention is an absorbent article that is used in abutment against a user's body, including: an absorbent body that has a longitudinal direction, a width direction perpendicular thereto, and a thickness direction perpendicular to the longitudinal direction, and that is positioned on a side close to the user's body in use; and an absorbent-article main body positioned farther from the user's body than the absorbent body, a face, on a side far from the user's body, of one end section of the absorbent body in the longitudinal direction and a face of the absorbent-article main body on the side close to the user's body being undetachably joined to each other, the absorbent article having a joined section in which a face, on the side far from the user's body, of another end section of the absorbent body in the longitudinal direction and the face of the absorbent-article main body on the side close to the user's body are detachably joined to each other inside an outer edge of the absorbent-body main body, the absorbent article having a non-joined section in which the absorbent body and the absorbent-article main body are not joined to each other between the joined section and the outer edge of the absorbent-article main body.

Effects of the Invention

According to the invention, it is possible to provide an absorbent article that is small and that can be easily worn by a user, and a method for producing the absorbent article.

LIST OF REFERENCE NUMERALS

Figure 1:
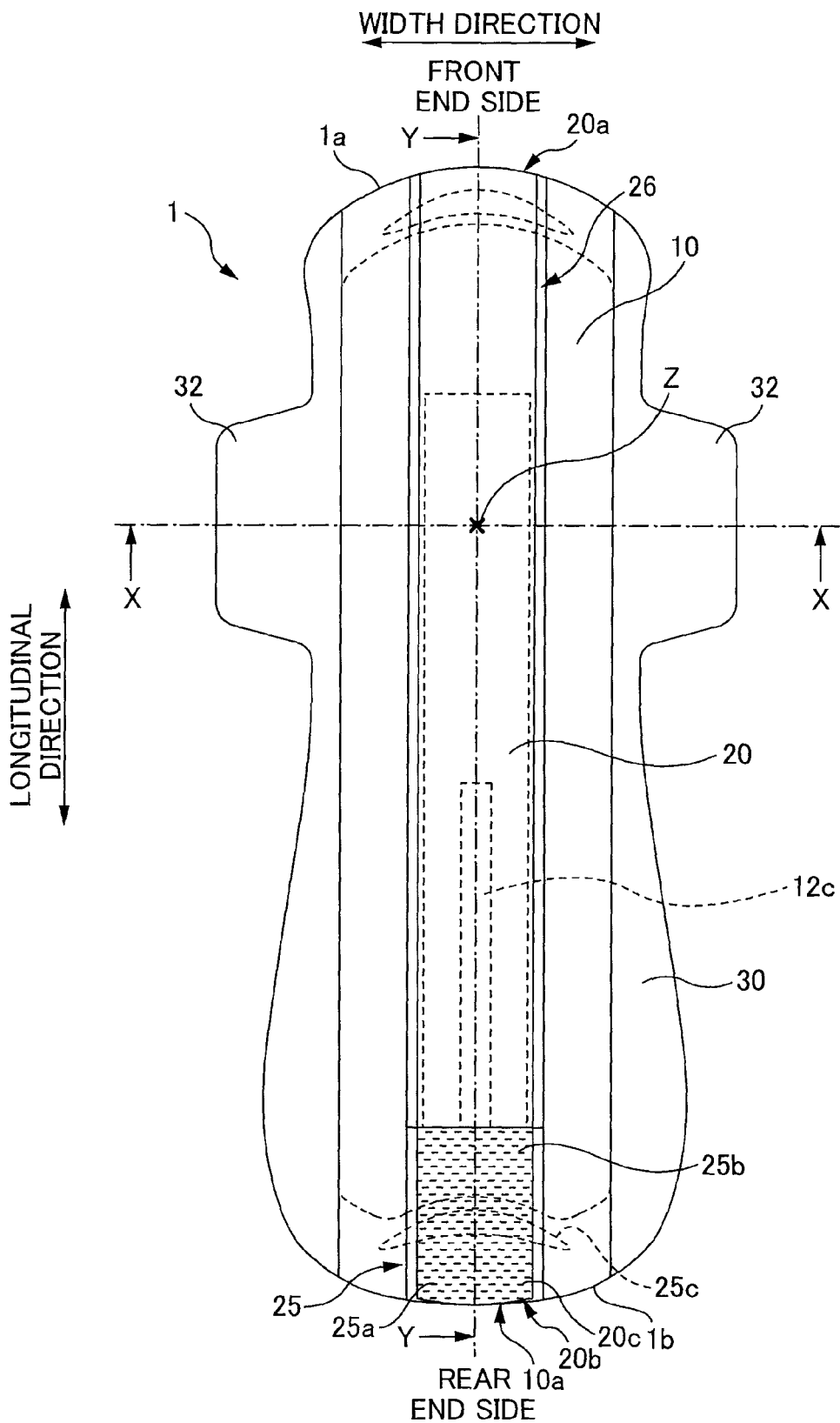
FIG. 1 is a plan view showing a surface side of an absorbent article according to the present embodiment.

1 . . . absorbent article, 1a . . . front end, 1b . . . rear end (outer edge), 2 . . . absorbent article, 3 . . . transporting apparatus, 4 . . . transporting apparatus, 10 . . . base absorbent body (absorbent-article main body), 10a . . . rear edge (outer edge), 11 . . . layered absorbent body, 12 . . . absorbent-body base material, 12a . . . absorbent-body material, 12b . . . thin paper, 12c . . . thin wall section, 12f . . . front end, 12g . . . rear end, 14 . . . surface sheet, 16 . . . intermediate sheet, 18 . . . groove section, 18a . . . first groove section, 18b . . . second groove section, 19 . . . deep concave section, 20 . . . top absorbent body (absorbent body), 20a . . . front end (one end section), 20b . . . rear end (the other end section), 20c . . . non-joined section, 21 . . . continuous body, 22 . . . hook member, 25 . . . reinforced section, 25a . . . handle section, 25c . . . temporarily joined section, 26 . . . reinforced section, 30 . . . back face sheet, 31 . . . joined section, 32 . . . holding section, 34 . . . release sheet, 35 . . . adhesive, 36 . . . wrapping sheet, 36a . . . front end, 36b . . . rear end, 36c . . . edge section, 38 . . . tape, 40 . . . revolving plate, Z . . . position assumed to abut against the bodily discharge opening section

BEST MODE FOR CARRYING OUT THE INVENTION

At least the following matters will be disclosed in the present specification and the drawings.

An absorbent article that is used in abutment against a user's body, including: an absorbent body that has a longitudinal direction, a width direction perpendicular thereto, and a thickness direction perpendicular to the longitudinal direction, and that is positioned on a side close to the user's body in use; and an absorbent-article main body positioned farther from the user's body than the absorbent body, a face, on a side far from the user's body, of one end section of the absorbent body in the longitudinal direction and a face of the absorbent-article main body on the side close to the user's body being undetachably joined to each other, the absorbent article having a joined section in which a face, on the side far from the user's body, of another end section of the absorbent body in the longitudinal direction and the face of the absorbent-article main body on the side close to the user's body are detachably joined to each other inside an outer edge of the absorbent-body main body, the absorbent article having a non-joined section in which the absorbent body and the absorbent-article main body are not joined to each other between the joined section and the outer edge of the absorbent-article main body.

With this sort of absorbent article, it is possible to detach the other end section of the absorbent body in the longitudinal direction from the absorbent-article main body, and to join the absorbent body to the absorbent-article main body only at the one end section in the longitudinal direction. That is to say, it is possible to use the absorbent article in a state where a portion on a side close to the other end section is separated from the absorbent-article main body. Furthermore, the other end section of the absorbent body has a non-joined section between a section where the absorbent body is detachably joined and the outer edge of the absorbent-article main body. Thus, an absorbent article can be realized in which the absorbent body can be lifted from a portion on a side close to the non-joined section to be easily detached from the absorbent-article main body. Herein, "joining" includes undetachable joining (hereinafter, also referred to as permanent joining) and detachable joining (hereinafter, also referred to as temporary joining).

In this absorbent article, it is desirable that the non-joined section is a handle section that is for being held by a user when detaching the absorbent body and the absorbent-article main body from each other.

With this sort of absorbent article, the non-joined section between the section where the absorbent body is detachably joined and the outer edge of the absorbent-article main body is configured as the handle section that is to be held by a user. Thus, an absorbent article can be provided in which a portion where the absorbent body and the absorbent-article main body are detachably joined can be easily detached from each other by a user holding the handle section.

Furthermore, a method for producing an absorbent article that is used in abutment against a user's body, including: a continuous-body production step that produces a continuous body in which absorbent bodies used for absorbing fluid and having a longitudinal direction, a width direction perpendicular thereto, and a thickness direction perpendicular to the longitudinal direction are continuously arranged; and a continuous-body joining step that undetachably joins a face on a side far from the user's body in one end section, in the longitudinal direction, of one of the absorbent bodies contained in the continuous body to a face on a side close to the user's body in use in an absorbent-article main body, and that detachably joins a face on the side far from the user's body in another end section, in the longitudinal direction, of that absorbent body to the face on the side close to the user's body in use in the absorbent-article main body, the continuous body being joined in the continuous-body joining step to the absorbent-article main body in such a manner as to have a non-joined section in which the absorbent body and the absorbent-article main body are not joined to each other between a detachably joined section of the continuous body and an outer edge of the absorbent article being produced.

With this sort of method for producing the absorbent article, in one absorbent body obtained by cutting the continuous body, the face on the side far from user's body in the one end section is undetachably joined to the face on the side close to the user's body in use in the absorbent-article main body, and the face on the side far from the user's body in the other end section is detachably joined to the face on the side close to the user's body in use in the absorbent-article main body. Thus, in the produced absorbent article, it is possible to detach the other end section from the absorbent-article main body, and to join the absorbent body to the absorbent-article main body only at the one end section. That is to say, it is possible to use the absorbent article in a state where the portion on the side close to the other end section is separated from the absorbent-article main body. Accordingly, for example, an absorbent article can be produced in which the absorbent body can be separated from the absorbent-article main body and placed in the groove between the buttocks to be in close contact with user's body in use. When this absorbent article is used, the other end section of the absorbent body has to be detached from the absorbent-article main body. Thus, according to the method for producing this absorbent article, in the continuous-body joining step, the continuous body is joined in such a manner as to have a non-joined section in which the absorbent body and the absorbent-article main body are not joined to each other between a section where the continuous body is detachably joined and the outer edge of the absorbent article to be produced. Thereby, a non-joined section is formed between the temporarily joined section in the absorbent body of the produced absorbent article and the outer edge of the absorbent article to be produced. Accordingly, an absorbent article can be produced in which the absorbent body and the absorbent-article main body can be easily detached from each other by a user holding the non-joined section. Herein, the end section refers to not only an edge of the outline section but also its vicinity including the edge. Accordingly, in the one end section that is undetachably joined and the other end section that is detachably joined, the edge is not necessarily joined. The same is applied to an "end section" in the following descriptions.

In this method for producing the absorbent article, it is desirable to further include a sheet-member joining step of joining the sheet member to another face of the absorbent-article main body along an external shape of the absorbent article.

With this sort of method for producing the absorbent article, in the sheet-member joining step, the sheet member is joined to the other face of the absorbent-article main body along the external shape of the absorbent article. Thus, leakage of fluid from the back face sides of the absorbent-article main body and the absorbent body can be suppressed with the sheet member. In particular, the sheet member is joined along the external shape of the absorbent article, and thus the rigidity of the external section of the absorbent article can be improved, and a tough absorbent article can be produced.

In this method for producing the absorbent article, it is desirable that in the sheet-member joining step, the other face of the absorbent-article main body and the sheet member are joined to each other by heat-pressing via an adhesive.

With this sort of method for producing the absorbent article, the other face of the absorbent-article main body and the sheet member are heat-pressed via an adhesive. Thus, the absorbent-article main body and the sheet member can be more firmly joined to each other along the external shape of the absorbent article, and the absorbent article having a tougher outer edge can be produced.

In this method for producing the absorbent article, it is desirable that in the continuous-body joining step, the one end section of the absorbent body in the longitudinal direction and the absorbent-article main body are joined to each other by compression-bonding via an adhesive.

With this sort of method for producing the absorbent article, the one end section in the longitudinal direction of one of the absorbent bodies contained in the continuous body and the absorbent-article main body are compression-bonded via an adhesive. Thus, the one end section in the longitudinal direction of the one absorbent body contained in the continuous body and the absorbent-article main body can be more firmly joined to each other such that they cannot be detached from each other.

In this method for producing the absorbent article, it is desirable to further include a reinforced section formation step that forms reinforced sections respectively at the one end section and the other end section of the absorbent body in the longitudinal direction by reinforcing the one end section and the other end section, wherein the reinforced section that is formed in the reinforced section formation step and is on a side close to the other end section is detachably joined to the absorbent-article main body in the continuous-body joining step, and the reinforced section that is formed in the reinforced section formation step and is on a side close to the one end section is undetachably joined to the absorbent-article main body in the continuous-body joining step.

With this sort of method for producing the absorbent article, a portion where one of the absorbent bodies contained in the continuous body is detachably joined in the continuous-body joining step is the reinforced section that has been reinforced in the reinforced section formation step. Thus, an absorbent article can be produced in which the absorbent body is unlikely to be damaged even when the detachably joined portion is detached.

Furthermore, a method for producing an absorbent article that is used in abutment against a user's body, including: a single-absorbent-body production step that produces as a discrete member an absorbent body used for absorbing fluid and having a longitudinal direction, a width direction perpendicular thereto, and a thickness direction perpendicular to the longitudinal direction; and an absorbent-body joining step that undetachably joins a face on a side far from the user's body in one end section of the absorbent body in the longitudinal direction to a face on a side close to the user's body in use in an absorbent-article main body, and that detachably joins a face on the side far from the user's body in another end section of the absorbent body in the longitudinal direction to the face on the side close to the user's body in use in the absorbent-article main body, the absorbent body being joined in the absorbent-body joining step to the absorbent-article main body in such a manner as to have a non-joined section in which the absorbent body and the absorbent-article main body are not joined to each other between a detachably joined section of the absorbent body and an outer edge of the absorbent article being produced.

With this sort of method for producing the absorbent article, in the absorbent body, the face on the side far from the user's body in the one end section is undetachably joined to the face on the side close to the user's body in use in the absorbent-article main body, and the face on the side far from the user's body in the other end section is detachably joined to the face on the side close to the user's body in use in the absorbent-article main body. Thus, in the produced absorbent article, it is possible to detach the other end section from the absorbent-article main body, and to join the absorbent body to the absorbent-article main body only at the one end section. That is to say, it is possible to use the absorbent article in a state where the portion on the side close to the other end section is separated from the absorbent-article main body. Accordingly, for example, he absorbent article can be produced in which the absorbent body can be separated from the absorbent-article main body and placed in the groove between the buttocks to be in close contact with user's body in use. When this absorbent article is used, the other end section of the absorbent body has to be detached from the absorbent-article main body. Thus, according to the method for producing this absorbent article, in the absorbent-body joining step, the absorbent body is joined in such a manner as to have a non-joined section in which the absorbent body and the absorbent-article main body are not joined to each other between a section where the absorbent body is detachably joined and the outer edge of the absorbent article to be produced. Thereby, the non-joined section is formed between the detachably joined section in the absorbent body of the produced absorbent article and the outer edge of the absorbent article to be produced. Accordingly, an absorbent article can be produced in which the absorbent body and the absorbent-article main body can be easily detached from each other by a user holding the non-joined section.

In this method for producing the absorbent article, it is desirable to further include a sheet-member joining step of joining the sheet member to the other face of the absorbent-article main body along an external shape of the absorbent article.

With this sort of method for producing the absorbent article, in the sheet-member joining step, the sheet member is joined to the other face of the absorbent-article main body along the external shape of the absorbent article. Thus, leakage of fluid from the back face sides of the absorbent-article main body and the absorbent body can be suppressed with the sheet member. In particular, the sheet member is joined along the external shape of the absorbent article, and thus the rigidity of the external section of the absorbent article can be improved, and a tough absorbent article can be produced.

In this method for producing the absorbent article, it is desirable that in the sheet-member joining step, the other face of the absorbent-article main body and the sheet member are joined to each other by heat-pressing via an adhesive.

With this sort of method for producing the absorbent article, the other face of the absorbent-article main body and the sheet member are heat-pressed via an adhesive. Thus, the absorbent-article main body and the sheet member can be more firmly joined to each other along the external shape of the absorbent article, and the absorbent article having a tougher outer edge can be produced.

In this method for producing the absorbent article, it is desirable that in the absorbent-body joining step, the one end section of the absorbent body in the longitudinal direction and the absorbent-article main body are joined to each other by compression-bonding via an adhesive.

With this sort of method for producing the absorbent article, the one end section in the longitudinal direction of the absorbent body and the absorbent-article main body are compression-bonded via an adhesive. Thus, the one end section in the longitudinal direction of the absorbent body and the absorbent-article main body can be more firmly joined to each other such that they cannot be detached from each other.

In this method for producing the absorbent article, it is desirable to further include a reinforced section formation step that forms reinforced sections respectively at the one end section and the other end section of the absorbent body in the longitudinal direction by reinforcing the one end section and the other end section, wherein the reinforced section that is formed in the reinforced section formation step and is on a side close to the other end section is detachably joined to the absorbent-article main body in the absorbent-body joining step, and the reinforced section that is formed in the reinforced section formation step and is on a side close to the one end section is undetachably joined to the absorbent-article main body in the absorbent-body joining step.

With this sort of method for producing the absorbent article, a portion where the absorbent body is detachably joined in the absorbent-body joining step is the reinforced section that has been reinforced in the reinforced section formation step. Thus, an absorbent article can be produced in which the absorbent body is unlikely to be damaged even when the detachably joined portion is detached. Furthermore, a portion where the absorbent body is undetachably joined in the absorbent-body joining step is the reinforced section that has been reinforced in the reinforced section formation step. Thus, an absorbent article can be produced in which the absorbent body is unlikely to be damaged even when the firmly joined portion is pulled.

In this method for producing the absorbent article, it is desirable that the absorbent-article main body includes another absorbent body that is different from the absorbent body.

With this sort of method for producing the absorbent article, the absorbent-article main body to which the absorbent body is joined further includes another absorbent body. Thus, even if fluid is not completely absorbed by the absorbent body, the fluid can be absorbed by the other absorbent body included in the absorbent-article main body.

Furthermore, an absorbent article that is produced by the above-mentioned method for producing the absorbent article.

With this sort of absorbent article, it is possible to detach the other end section of the absorbent body from the absorbent-article main body, and to join the absorbent body to the absorbent-article main body only at the one end section. That is to say, it is possible to use the absorbent article in a state where the portion on the side close to the other end section is separated from the absorbent-article main body. Moreover, the absorbent body and the absorbent-article main body can be easily detached from each other by holding the non-joined section on the side close to another edge in the absorbent body.

First Embodiment

First, the outline of the configuration of an absorbent article according to a first embodiment will be described. The absorbent article of this embodiment is a sanitary napkin. In the following description, a side that is brought into contact with a body is referred to as a surface side, a side that is brought into contact with an undergarment is referred to as a back face side, an end that is positioned on the front side of the human body when worn is referred to as a front end, and an end that is positioned on the rear side is referred to as a rear end.

Figure 2:
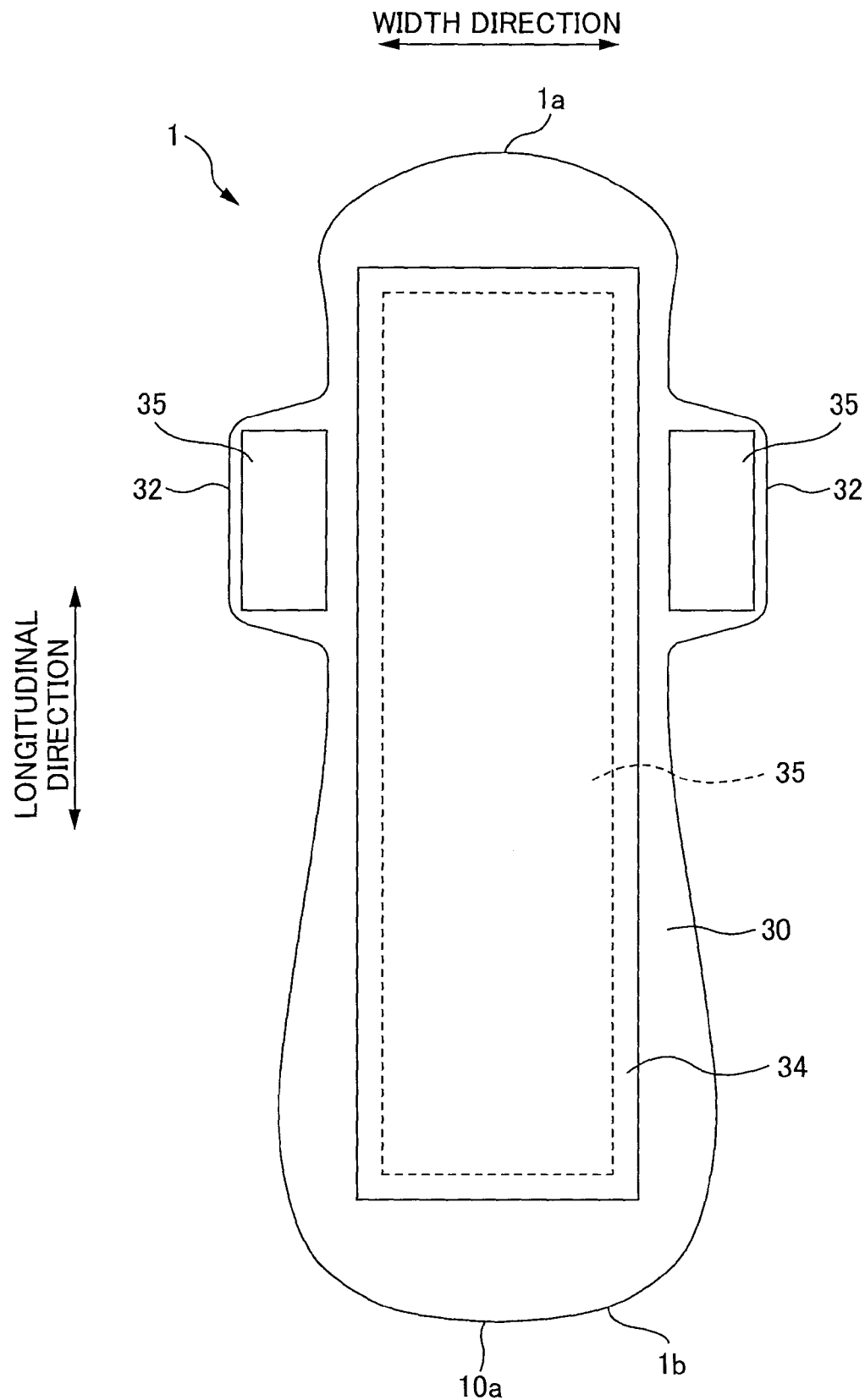
FIG. 2 is a view showing a back face side of the absorbent article according to this embodiment.
Figure 3:
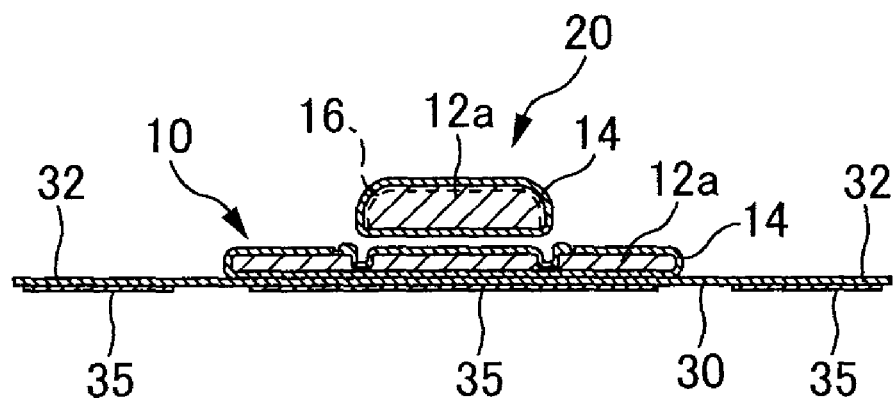
FIG. 3 is a cross-sectional view taken along line X-X in FIG. 1.
Figure 4:
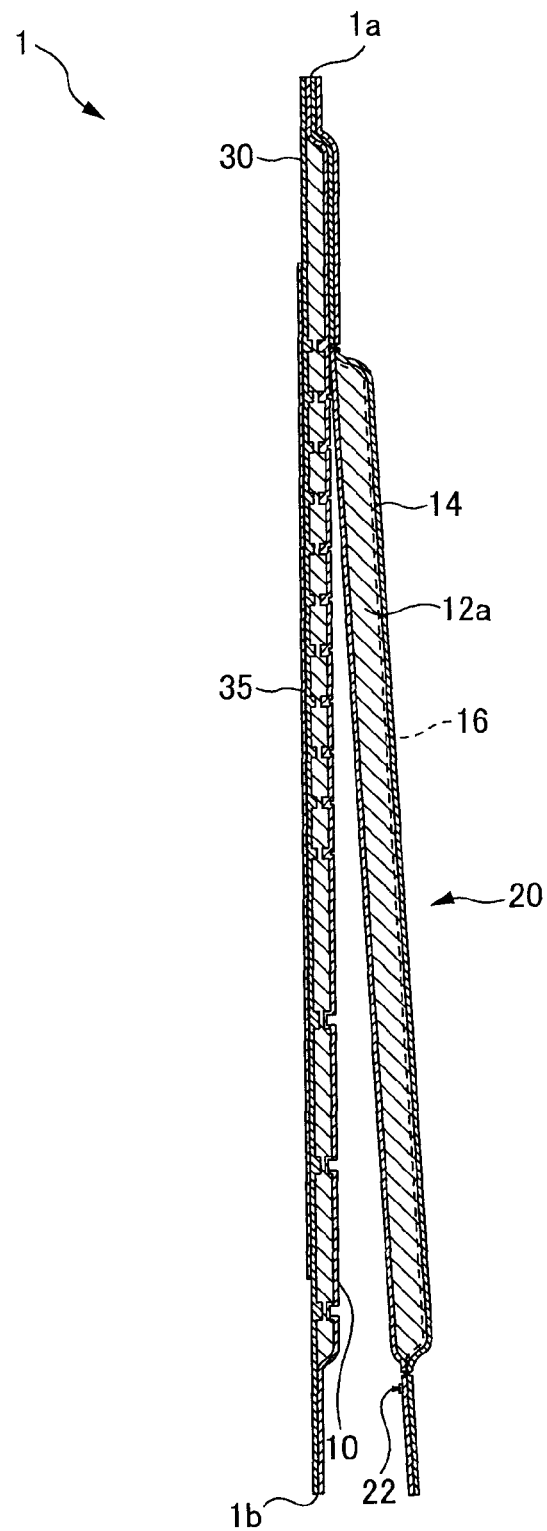
FIG. 4 is a cross-sectional view taken along line Y-Y in FIG. 1.
Figure 5:
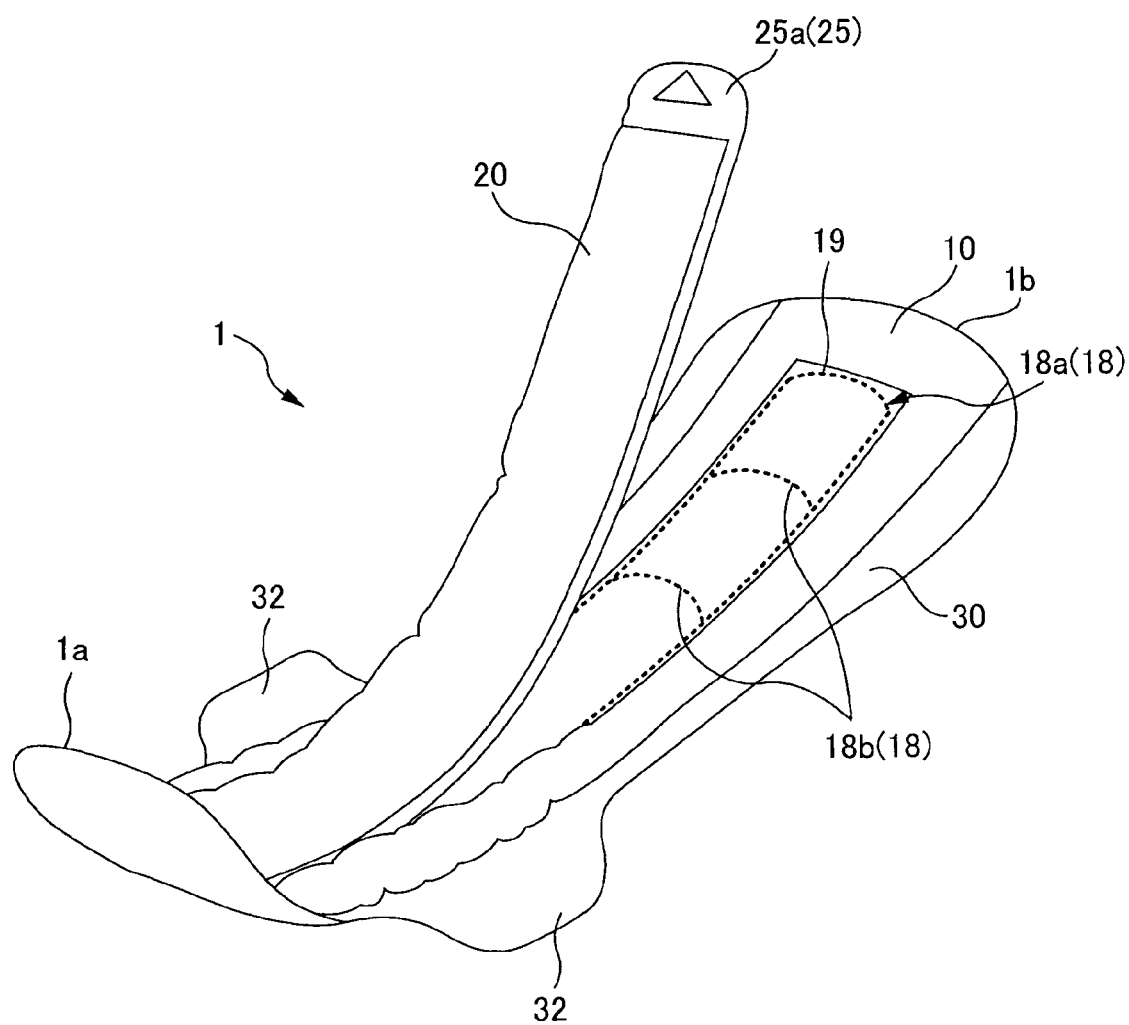
FIG. 5 is a perspective view showing the absorbent article according to this embodiment.
Figure 6:
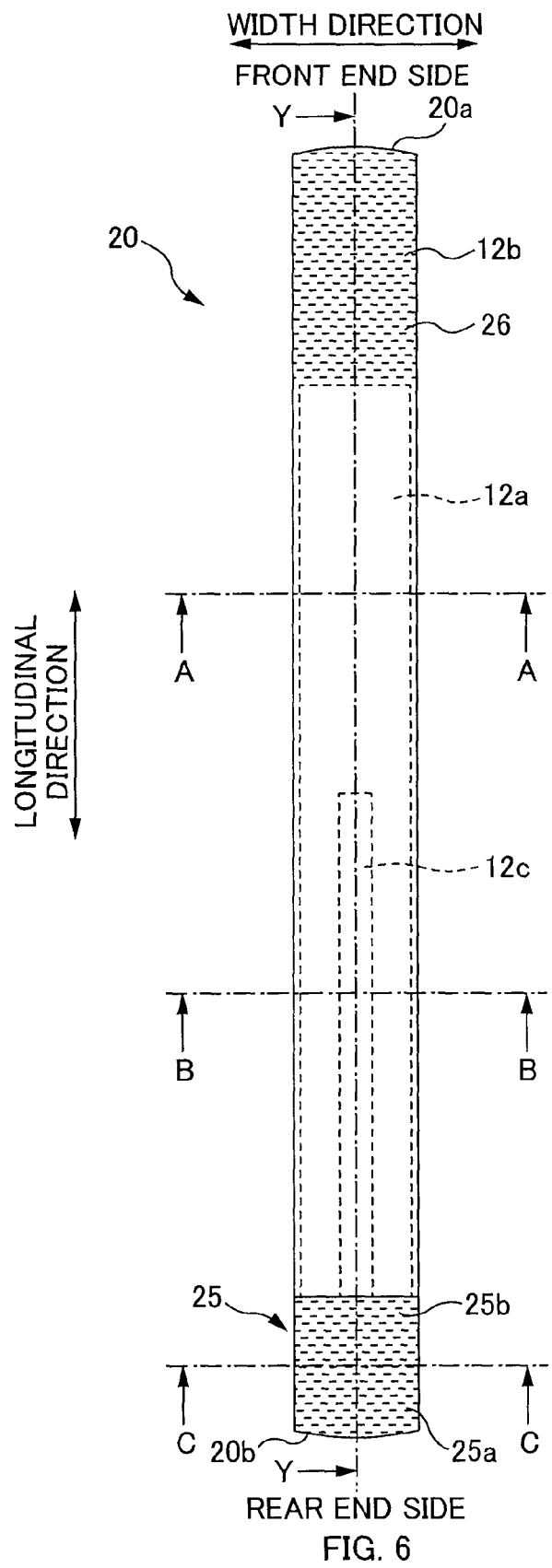
FIG. 6 is a plan view showing a top absorbent body.
Figure 7A:
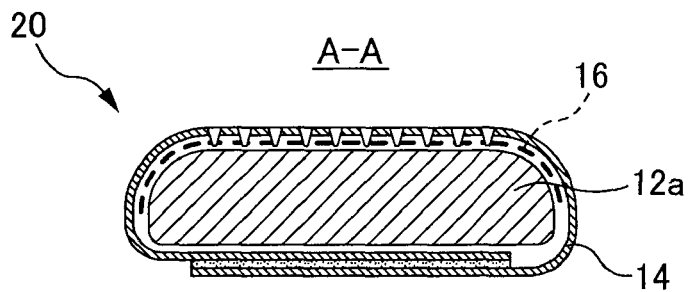
FIG. 7(a) is a cross-sectional view taken along line A-A in FIG. 6.
Figure 7B:
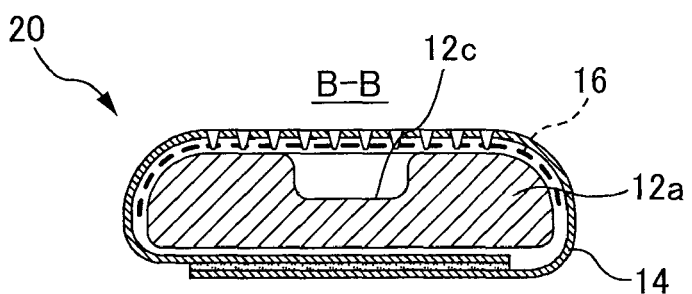
FIG. 7(b) is a cross-sectional view taken along line B-B in FIG. 6.
Figure 7C:
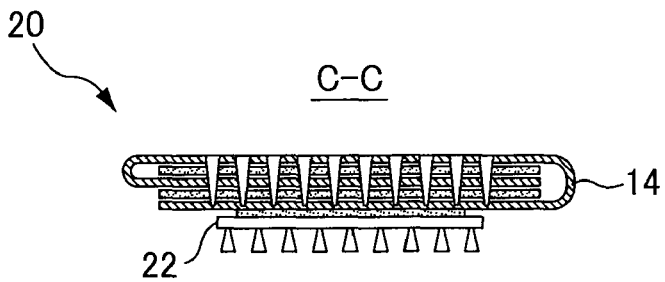
FIG. 7(c) is a cross-sectional view taken along line C-C in FIG. 6.

FIG. 1 is a plan view showing the surface side of the absorbent article according to this embodiment. FIG. 2 is a view showing the back face side of the absorbent article according to this embodiment. FIG. 3 is a cross-sectional view taken along line X-X in FIG. 1. FIG. 4 is a cross-sectional view taken along line Y-Y in FIG. 1. FIG. 5 is a perspective view showing the absorbent article according to this embodiment. FIG. 6 is a plan view showing a top absorbent body. FIG. 7(*a*) is a cross-sectional view taken along line A-A in FIG. 6. FIG. 7(*b*) is a cross-sectional view taken along line B-B in FIG. 6. FIG. 7(*c*) is a cross-sectional view taken along line C-C in FIG. 6.

Absorbent Article

As shown in the figures, an absorbent article 1 in this embodiment is elongated in a predetermined direction. The absorbent article 1 includes: a base absorbent body 10 that is a substantially rectangular absorbent-article main body for absorbing fluid such as menstrual blood; a top absorbent body 20 that is an absorbent body joined to a surface, which is one face of the base absorbent body 10, and that is disposed along a longitudinal direction in a middle in a width direction of the base absorbent body 10; and a back face sheet 30 that is a sheet member provided on a back face, which is the other face of the base absorbent body 10. The back face sheet 30 is provided in order to prevent fluid that is to be absorbed by the base absorbent body 10 and the top absorbent body 20 from leaking to the back face side.

In the absorbent article 1, a position Z assumed to abut against the bodily discharge opening section, at which the bodily discharge opening section is assumed to abut against the absorbent article 1, is positioned closer to the front end than a middle in the longitudinal direction, on a center line in a width direction of the absorbent article 1. More specifically, the absorbent article 1 is formed such that a length from the position Z assumed to abut against the bodily discharge opening section to the rear end side is longer than a length from the position Z assumed to abut against the bodily discharge opening section to the front end side.

The base absorbent body 10 includes: an absorbent-body base material 12 that serves as another absorbent body in a form of a sheet having a predetermined thickness, in which an absorbent-body material 12a (FIG. 11) that has pulverized pulp obtained by pulverizing sheet-like pulp, a superabsorbent polymer, and a heat-fusible fiber is wrapped in thin paper 12b (FIG. 11) such as tissue paper; and a surface sheet 14 that is attached to a surface of a middle section in a width direction of the absorbent-body base material 12. The absorbent-body material 12a is substantially rectangular as described above, but its rear end side is curved in the middle in the width direction toward its front end side as shown in FIG. 1. Both of the thin paper 12b and the surface sheet 14 are fluid-permeable sheets. Furthermore, the thin paper 12b is a sheet having openings that are smaller than particles of the superabsorbent polymer, and prevents the superabsorbent polymer from leaking out of the absorbent-body base material 12. The surface sheet 14 is a sheet that is softer than the thin paper 12b, because it is positioned on the surface side, which is brought into contact with user's body.

In a similar manner as the base absorbent body 10, the top absorbent body 20 includes the absorbent-body material 12a, which is made of pulverized pulp, a superabsorbent polymer, and a heat-fusible fiber. The top absorbent body 20 also includes a fluid-permeable intermediate sheet 16 on the surface side, which is brought into contact with user's body, and the intermediate sheet 16 can retain more fluid than the surface sheet 14. The exterior of the top absorbent body 20 is wrapped around by a surface sheet 14 as included in the base absorbent body 10. The intermediate sheet 16 is a member that is denser than the surface sheet 14 and is highly absorptive due to surface tension. The intermediate sheet 16 is provided inside the surface sheet 14, so that fluid that has permeated the surface sheet 14 is moved toward the intermediate sheet 16, which draws fluid more than the surface sheet 14.

The top absorbent body 20 is formed having a width narrower than the base absorbent body 10, and is formed such that when the top absorbent body 20 is disposed on the base absorbent body 10 in the longitudinal direction and joined thereto, a rear edge of the top absorbent body 20 is substantially matched to a rear edge of the base absorbent body 10. Furthermore, in a middle section in a width direction of the top absorbent body 20, a thin wall section 12c is formed along the longitudinal direction in a substantially half region on the rear end side, as shown in FIG. 7(b), the thin wall section 12c containing a smaller amount of the absorbent-body material 12a than in other portions. With the thin wall section 12c, the top absorbent body 20 can be easily bent in the longitudinal direction such that the surface side continuously forms a peak.

Furthermore, on sides respectively close to a front end 20a and a rear end 20b of the top absorbent body 20, reinforced sections 25 and 26 are formed that have been reinforced by folding the surface sheet 14 only and performing embossing in a state where an adhesive exists between the folded sections of the surface sheet 14. The reinforced sections 25 and 26 do not contain any of the absorbent-body material 12a and the intermediate sheet 16. The embossing will be described later.

A portion on the front end 20a side, which serves as one end section of the top absorbent body 20, is permanently joined to the base absorbent body 10 at the reinforced section 26, and a portion on the rear end 20b side, which serves as the other end section, is formed such that the portion can separate from the base absorbent body 10. Before use, the reinforced section 25 is temporarily joined to the portion on the rear end 20b side in the top absorbent body 20, at an area inside the rear edge of the base absorbent body 10. The top absorbent body 20 has a non-joined section 20c in which the top absorbent body 20 and the base absorbent body 10 are not joined to each other, between a temporarily joined section 25c that has been temporarily joined and a rear edge 10a of the base absorbent body 10 serving as an outer edge of the absorbent article 1. The non-joined section 20c serves as a handle section 25a that can be held by the user, for example, who is going to wear the absorbent article 1. Herein, permanent joining refers to an undetachable state in which the top absorbent body 20 and the base absorbent body 10 are firmly joined to each other such that at least either one of the top absorbent body 20 and the base absorbent body 10 is inevitably broken if the top absorbent body 20 and the base absorbent body 10 are to be separated from each other. Temporary joining refers to a detachable state in which the base absorbent body 10 and the top absorbent body 20 are joined to each other such that the user can detach and easily separate the top absorbent body 20 from the base absorbent body 10 without impairing the function of the base absorbent body 10 and the top absorbent body 20. In the following description, an end section refers to not only an edge of an outline section but also the edge and its vicinity. Accordingly, in the permanently joined one end section and the temporarily joined other end section, the edge is not necessarily joined.

Furthermore, in the reinforced section 25 on the rear end 20b side, at a position that opposed to the base absorbent body 10 and where a section 25b exists that is closer to the absorbent-body material 12a than the position where temporarily joined to the base absorbent body 10, a hook member 22 is provided for fixing the portion on the rear end 20b side in the top absorbent body 20 to an undergarment in use. The hook member 22 is, for example, a male member of a mechanical fastener. The base absorbent body 10 and the reinforced section 25 on the rear end 20b side in the top absorbent body 20 superpose and are temporarily joined by compression-bonding by embossing. Further, the hook member 22 functions to temporarily join the portion on the rear end 20b side in the top absorbent body 20 and the surface sheet 14 of the base absorbent body 10 before use. Note that the hook section member 22 does not necessarily have to be provided in the reinforced section 25. For example, the hook member 22 may be provided along the longitudinal direction on a portion in which the absorbent-body material 12a of the top absorbent body 20 is disposed. The use of the hook member 22 for temporary joining is described above, but the method for temporary joining is not limited thereto. For example, the components may be joined by only compression-bonding by embossing, or may be caused to adhere instead of using the hook member 22.

The back face sheet 30 is a thermoplastic and fluid-impermeable sheet made of materials such as polyethylene or polypropylene. The back face sheet 30 is formed sufficiently wider than the base absorbent body 10. Furthermore, on both sides in the width direction, holding sections 32 extending outward in the width direction are formed in a predetermined region centering, in the longitudinal direction, on the position Z assumed to abut against the bodily discharge opening section. On the back face side on the back face sheet 30, release sheets 34 (FIGS. 2 and 8) are provided via adhesives 35 in the holding sections 32 and in the vicinity of a region whose surface side has the base absorbent body 10. When the absorbent article 1 is used, the release sheets 34 are removed, and the back face sheet 30 abuts against an inner side on an undergarment. Also, the holding sections 32 are folded outward, and abut against an outer face of the undergarment. With the adhesives 35 between the back face sheet 30 and the undergarment, the absorbent article 1 is held on the undergarment. Note that a release agent has been applied to the release sheets 34, and thus the release sheets 34 can be easily removed from the adhesives. In this embodiment, the back face sheet 30 as a sheet member is a thermoplastic and fluid-impermeable sheet made of materials such as polyethylene or polypropylene. However, the back face sheet 30 may be a sheet-like member containing a thermoplastic and fluid-impermeable sheet formed by layering thin paper, nonwoven fabric, or the like.

Figure 8:
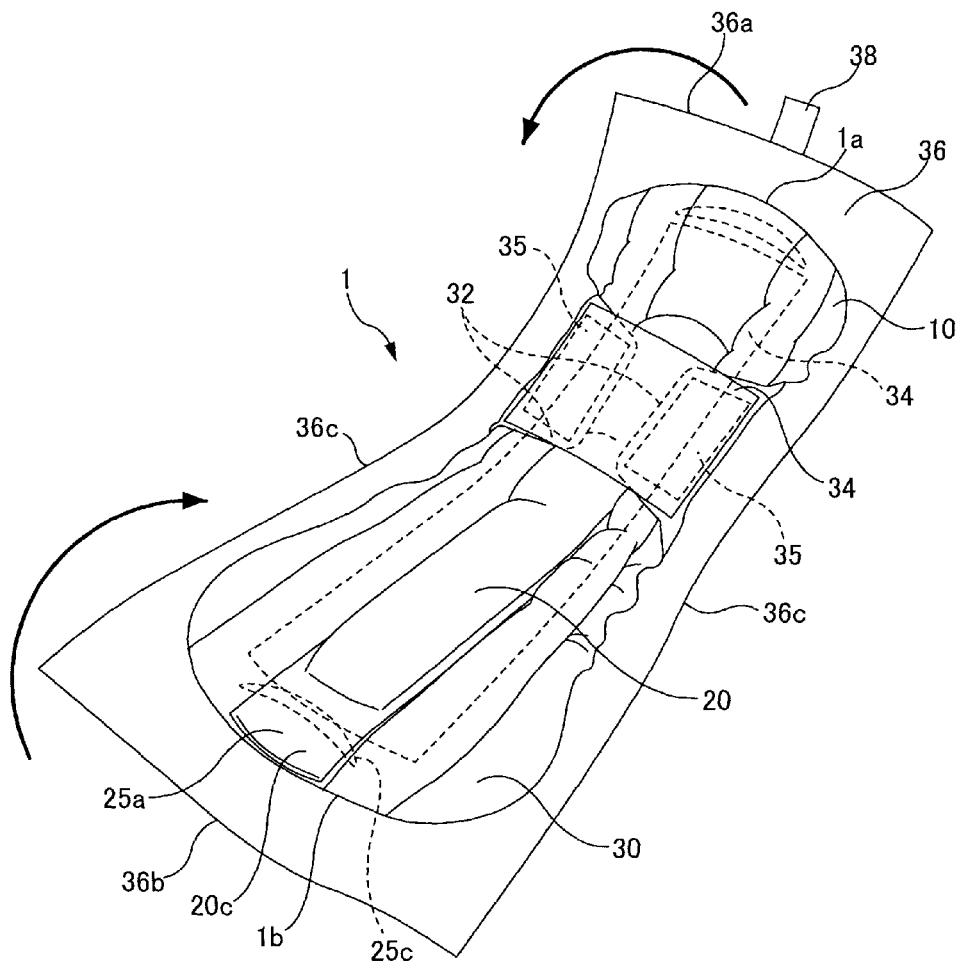
FIG. 8 is a diagram for illustrating a state in which the absorbent article is wrapped.

Next, the absorbent article 1 in a wrapped state will be described. FIG. 8 is a diagram for illustrating a state in which the absorbent article is wrapped.

In the wrapped absorbent article 1, the holding sections 32 are bent toward the surface side, and the release sheets 34 covering the adhesives 35 are provided on the holding sections 32 on both sides and the back face side. The absorbent article 1 on which the release sheets 34 have been placed is folded toward the surface side so as to be rolled up along the longitudinal direction together with a rectangular wrapping sheet 36 disposed on the back face side. At this time, an end section of the wrapping sheet 36 on a side close to a rear end 1b of the absorbent article 1 (hereinafter, referred to as a rear end 36b of the wrapping sheet 36) is extended to be longer than the absorbent article 1, and an adhesive has been slightly applied to the end section. When the wrapping sheet 36 is bent together with the absorbent article 1, the end section adheres with very slight adhesion to a not-detachment-processed surface of the release sheet 34, that is not processed treatment for detachment on, the release sheet 34 being provided on the holding sections 32 that have been folded toward the surface side of the top absorbent body 20. A tape 38 provided on a side close to a front end 36a in the wrapping sheet 36 is attached to an outer face, on the side close to the rear end 36b, of the wrapping sheet 36 that has been already bent together with the absorbent article 1. The wrapping sheet 36 that has been bent together with the absorbent article 1 is sealed by causing edge sections 36c in the longitudinal direction to adhere, and the absorbent article 1 that is contained in the wrapping sheet 36 in the form of a package is supplied to the user.

When the user removes the tape 38 of the wrapped absorbent article 1 and opens the wrapping sheet 36, a front end 1a is exposed. When the exposed front end 1a of the absorbent article 1 is peeled from the wrapping sheet 36 having the tape 38, the absorbent article 1 can be easily taken out. The taken out absorbent article 1 is disposed at an appropriate position on an undergarment after the release sheet 34 on the back face side is removed. Then, the release sheet 34 on the holding sections 32 is removed, and the holding sections 32 are bent toward the undergarment. The holding sections 32 are attached to an outer side on the undergarment with the adhesives 35, and thus the absorbent article 1 is fixed to the undergarment. After the undergarment to which the absorbent article 1 is fixed is pulled up toward user's body, the handle section 25a in the non-joined section 20c, which has not been joined to the base absorbent body 10, in the reinforced section 25 of the top absorbent body 20 is held and the top absorbent body 20 is pulled up by the user. Accordingly, the temporary joining between the base absorbent body 10 and the top absorbent body 20 is cancelled, and the portion on the rear end 20b side in the top absorbent body 20 is moved apart from the base absorbent body 10.

Subsequently, when the user moves the handle section 25a in the longitudinal direction (substantially the vertical direction), a position of the top absorbent body 20 is adjusted so that the top absorbent body 20 is in close contact with the bodily groove at the bodily discharge opening section and its vicinity. After the position has been adjusted, the top absorbent body 20 is bent and fixed at the skin-side surface of a back body of the undergarment or an edge section of the undergarment. Accordingly, the top absorbent body 20 is positioned so as to preferably abut against user's body. At that time, if the hook member 22 is provided not on the rear end side in the top absorbent body 20 but on a lower side in a portion that is in the top absorbent body 20 and that includes the absorbent-body material 12a, the hook member 22 may be fixed to the base absorbent body 10. Furthermore, if the base absorbent body 10 is longer than the top absorbent body 20, the rear end side in the top absorbent body 20 whose position is adjusted may be fixed to the base absorbent body 10, if necessary.

Method for Producing Absorbent Article

Figure 9:
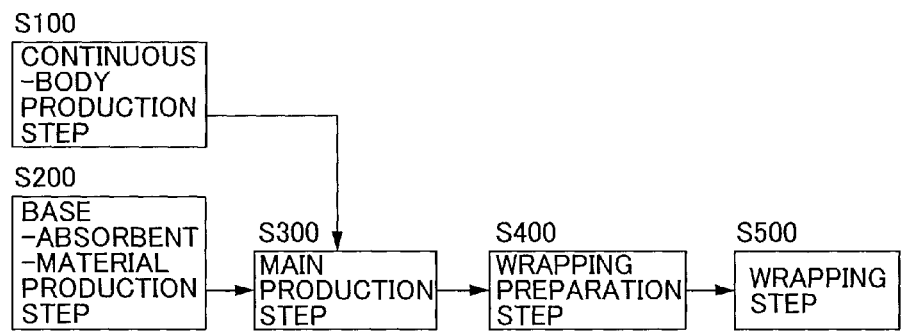
FIG. 9 is a diagram for illustrating a method for producing the absorbent article according to a first embodiment.

Next, a method for producing the absorbent article 1 will be described. FIG. 9 is a diagram for illustrating steps of producing the absorbent article.

A first embodiment of the method for producing the absorbent article 1 includes: a continuous-body production step S100 of producing a continuous body 21 in which the top absorbent bodies 20 are continuously arranged; a base-absorbent-body production step S200 of producing the base absorbent body 10; a main production step S300 of producing the absorbent article 1 using the base absorbent body 10 and the continuous body 21; a wrapping preparation step S400 of preparing the absorbent article 1 for wrapping; and a wrapping step S500 of wrapping the absorbent article 1.

Figure 10:
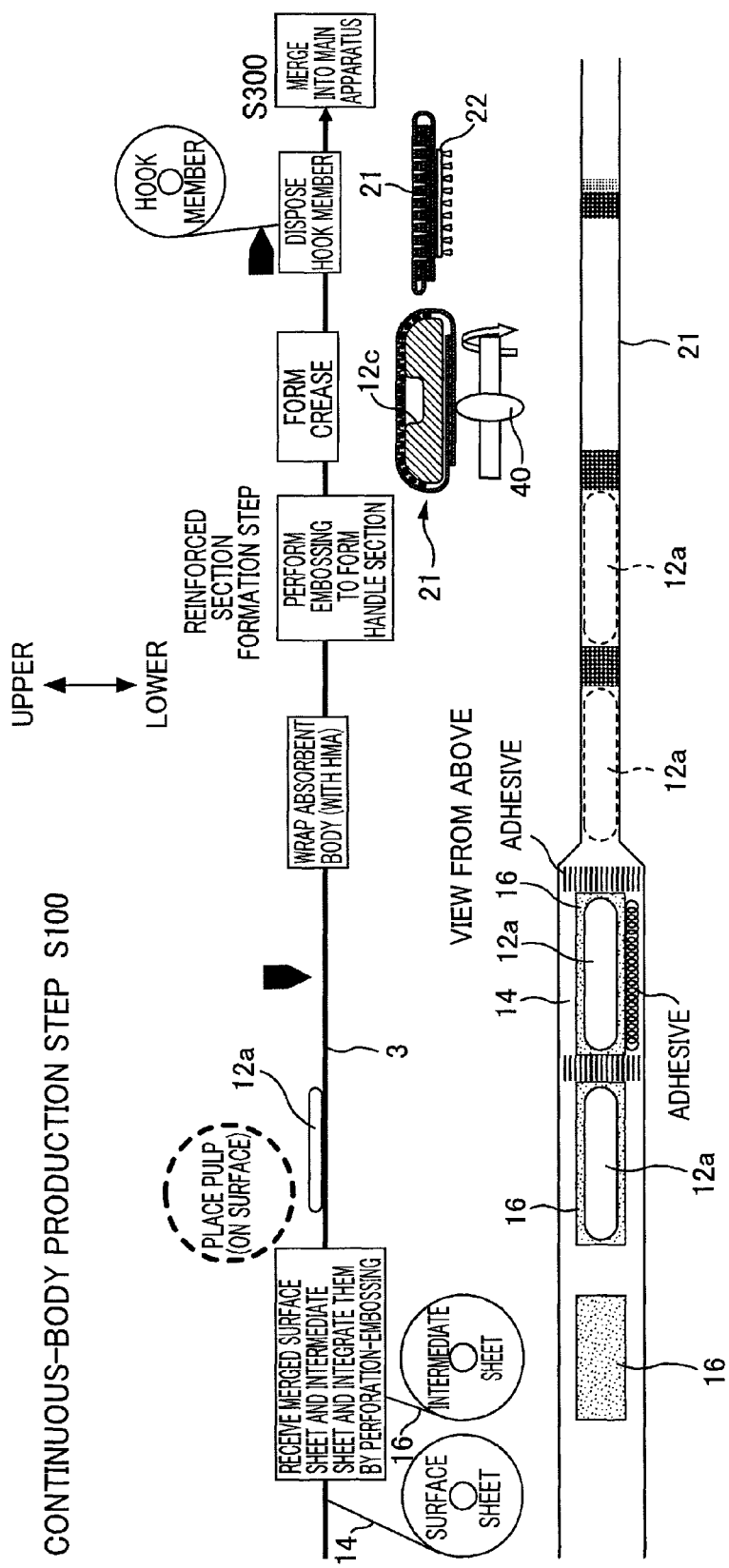
FIG. 10 is a diagram for illustrating a continuous-body production step.
Figure 11:
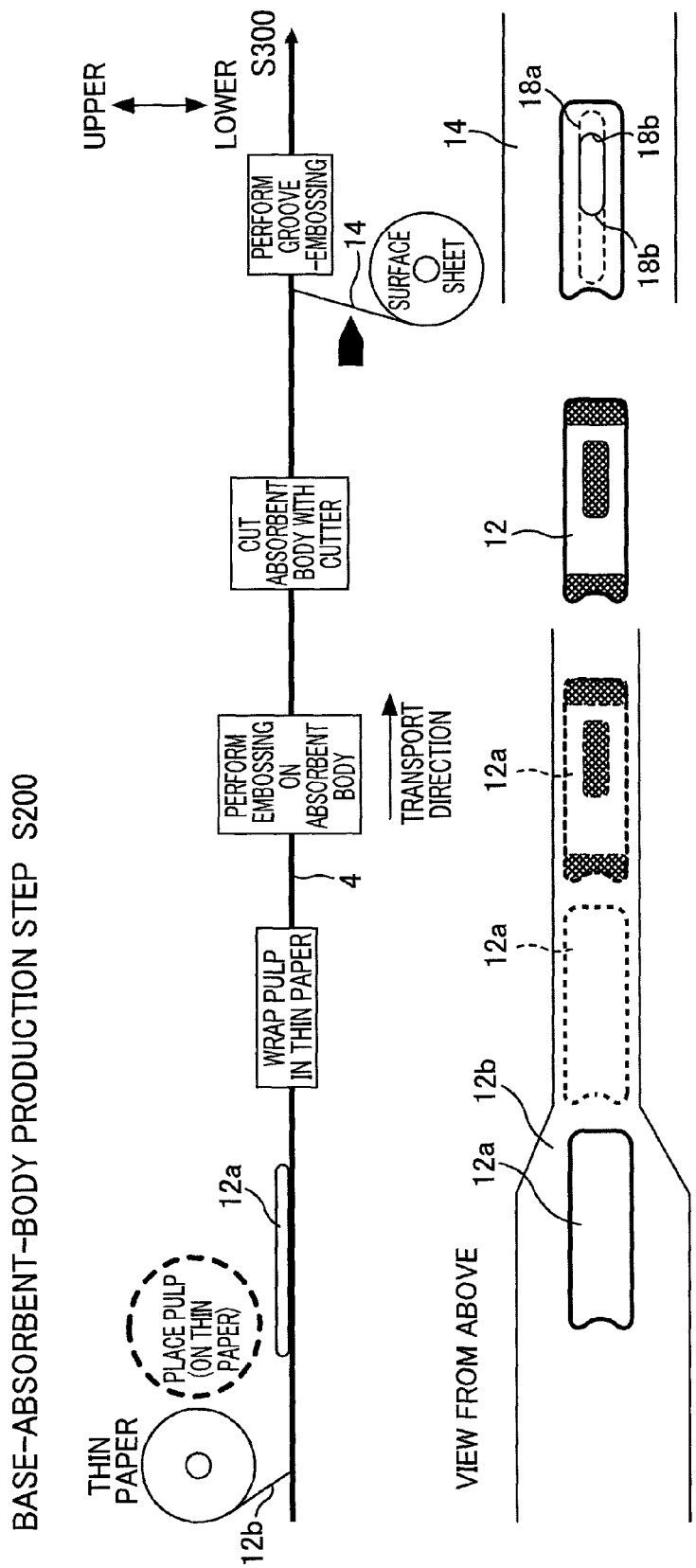
FIG. 11 is a diagram for illustrating a base-absorbent-body production step.
Figure 12:
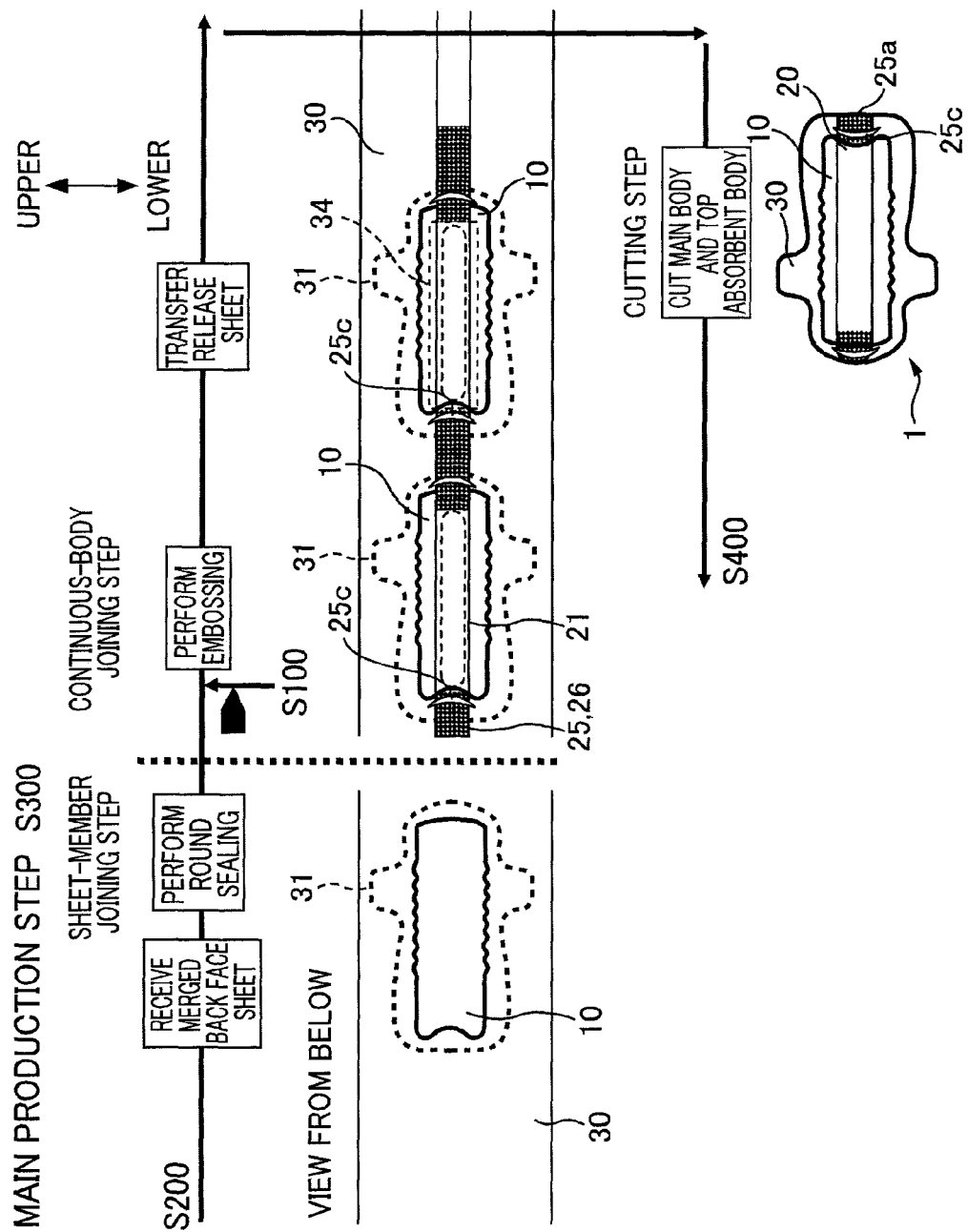
FIG. 12 is a diagram for illustrating a main production step.
Figure 13:
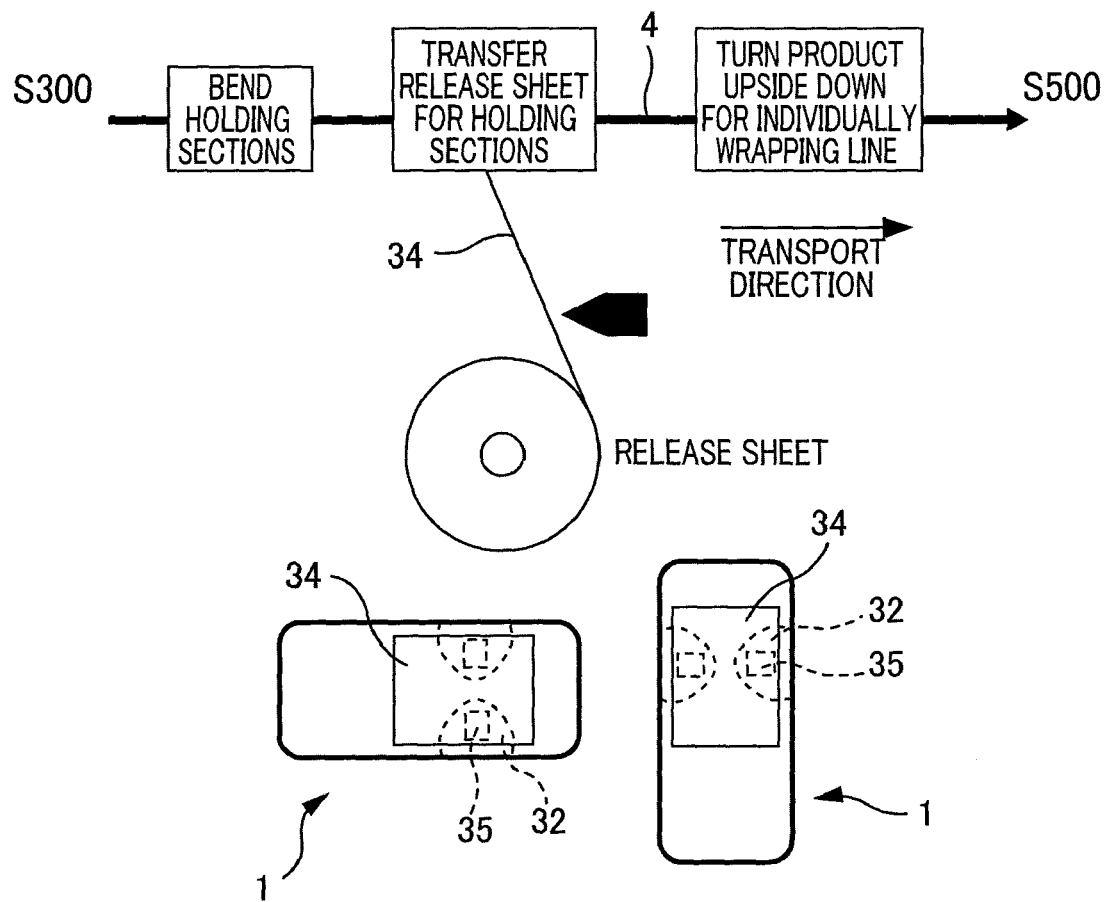
FIG. 13 is a diagram for illustrating a wrapping preparation step.
Figure 14:
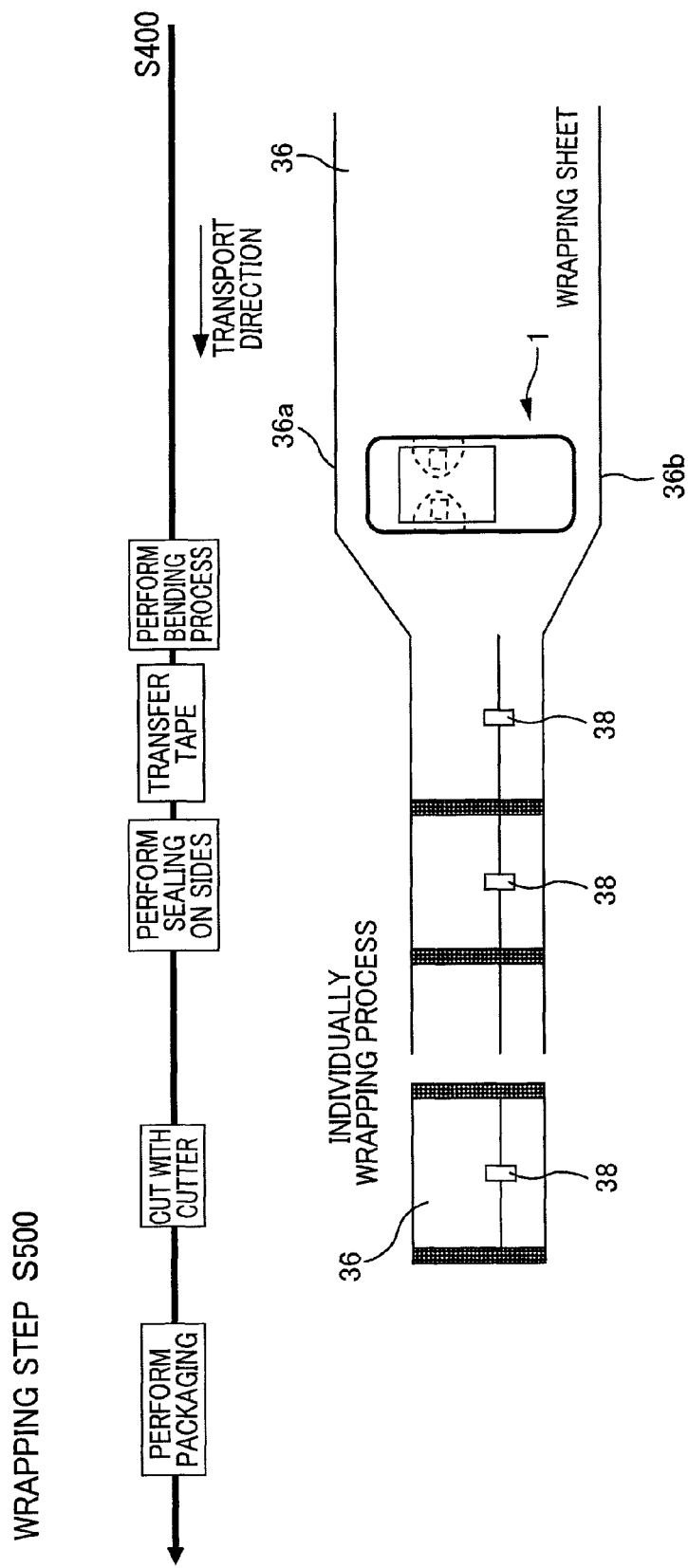
FIG. 14 is a diagram for illustrating a wrapping step.

FIG. 10 is a diagram for illustrating the continuous-body production step. FIG. 11 is a diagram for illustrating the base-absorbent-body production step. FIG. 12 is a diagram for illustrating the main production step. FIG. 13 is a diagram for illustrating the wrapping preparation step. FIG. 14 is a diagram for illustrating the wrapping step. In FIGS. 10 to 14, the flow of each production step is shown in the upper level, and images of the article that is being produced are shown in the lower level. In production, the absorbent article 1 is produced while materials and products are placed on and transported by a transporting apparatus such as a conveyer.

Continuous-Body Production Step S100

As shown in FIG. 10, the belt-like surface sheet 14 that has been wound in a roll is supplied onto a transporting apparatus 3 for producing a continuous body. When the surface sheet 14 is transported, air is sucked from below the transporting apparatus 3, and thus the surface sheet 14 is drawn toward the transporting apparatus 3.

The intermediate sheet 16 that has been cut in the form of a single sheet is supplied onto the transported surface sheet 14, and the surface sheet 14 and the intermediate sheet 16 are integrated by perforation-embossing. Perforation-embossing is performed by these sheets passing through between two rollers (not shown) that vertically oppose each other. For example, one of the rollers used for the perforation-embossing has protrusions in the form of cones, and the opposing roller has holes into which the conical protrusions are inserted. The roller having the protrusions is heated. Thus, when the conical protrusions pass through the surface sheet 14 and the intermediate sheet 16 and openings are formed, edge sections of the openings are thermally welded. As a result thereof, the surface sheet 14 and the intermediate sheet 16 are integrated.

When the surface sheet 14 and the intermediate sheet 16 that have been integrated are transported, the absorbent-body material 12a in which pulverized pulp supplied from an apparatus for pulverizing sheet-like pulp, a superabsorbent polymer, and a heat-fusible fiber are mixed is formed in a predetermined form, and is layered on the intermediate sheet 16. At that time, the absorbent-body materials 12a are transported while being placed on the intermediate sheets 16 that are spaced away from each other in the transport direction on the surface sheets 14 that are continuously supplied.

A hot-melt adhesive is applied to the surface sheets 14 that are continuously transported, at portions between the adjacent absorbent-body materials 12a, and at portions next to the absorbent-body material 12a in the width direction (the direction that intersects the transport direction).

A surface of the transporting apparatus 3 is bent such that the surface sheet 14 is guided to wrap around the absorbent-body material 12a when a layered absorbent body 11 formed by layering the surface sheet 14 to which the hot-melt adhesive has been applied, the intermediate sheet 16, and the absorbent-body material 12a is transported. When the surface sheet 14 is guided along the bent surface of the transporting apparatus 3, the absorbent-body material 12a is wrapped in the surface sheet 14 integrated with the intermediate sheet 16. In this embodiment, a side serving as a surface of the absorbent article 1 as a final product faces the transporting apparatus 3. Accordingly, when the absorbent-body material 12a is wrapped in the surface sheet 14, end sections in the width direction of the surface sheet 14 are overlapped and adhere to each other above the absorbent-body material 12a, and the surface sheet 14 is formed into a tube. At that time, the absorbent-body materials 12a are supplied to the transporting apparatus 3 at predetermined intervals, and a plurality of absorbent-body materials 12a are successively arranged having a spacing therebetween in the tubular surface sheets 14.

Next, embossed patterns are formed by performing embossing on portions between the adjacent absorbent-body materials 12a that have been wrapped in the surface sheets 14, and thus the portions are caused to adhere. Embossing is performed by causing a product to pass through between two rollers that vertically oppose each other, in the same manner as the above-described perforation-embossing. On a lower roller provided on a side close to the transporting apparatus 3, protrusions are formed on a portion that abuts against a region of the absorbent-body material 12a at which an embossed pattern is to be formed when the absorbent-body material 12a has been transported to that portion. A surface of an upper roller opposed to the lower roller is flat. At that time, the front ends of the protrusions are flat, and thus concave sections having flat bottom sections are formed on the surface sheet 14. When the absorbent-body materials 12a wrapped in the surface sheets 14 that have been integrated with the intermediate sheets 16 pass through between the upper roller and the lower roller, the protrusions compress portions between the adjacent absorbent-body materials 12a. The portions between the absorbent-body materials 12a that have been compressed by the protrusions adhere and are sealed, and the sealed sections serve as the reinforced sections 25 and 26. Thus, the continuous body 21 of the top absorbent bodies 20 is produced in which the reinforced sections 25 and 26 are formed respectively at the front and rear of each absorbent-body material 12a (Reinforced Section Formation Step).

The continuous body 21 is further transported, and a crease is formed along the thin wall section 12c of the absorbent-body material 12a. The crease is formed in order to make the top absorbent body 20 easily bendable substantially in the middle in the width direction such that the top absorbent body 20 is brought into close contact with the bodily groove in the vicinity of the bodily discharge opening section. With this processing of forming a crease, the crease is formed such that the absorbent article 1 is naturally bent in the middle in the width direction when worn. The crease is formed when the absorbent-body materials 12a successively arranged on the surface sheets 14 pass on a disk-like revolving plate 40 that is supported on a shaft in the width direction and that rotates in the transport direction of the transporting apparatus 3 as shown in FIG. 10. At that time, the revolving plate 40 is brought into contact with a side on which the surface sheet 14 is overlapped, only at the thin wall section 12c of the absorbent-body material 12a in the transport direction and its vicinity.

Subsequently, the hook member 22 is supplied to a portion that is to serve as each of the top absorbent bodies 20 of the continuous body 21. At that time, hot-melt adhesive has been applied to a back face of the hook member 22. The hook member 22 adheres to either one of the reinforced sections 25 and 26 that are arranged at the front and rear in the transport direction of each of the top absorbent bodies 20. In this embodiment, the absorbent article 1 is transported such that the front end 1a thereof is positioned on the front side in the transport direction, and thus the hook member 22 adheres to the reinforced section 25 that is positioned on the rear side in the transport direction. The continuous body 21 is supplied in this state to the main production step S300.

Base-Absorbent-Body Production Step S200

The base-absorbent-body production step S200 is performed on a transporting apparatus 4 different from that in the continuous-body production step S100.

As shown in FIG. 11, the belt-like thin paper 12b that has been wound in a roll is pulled out and supplied onto the transporting apparatus 4.

The absorbent-body material 12a in which pulverized pulp supplied from an apparatus for pulverizing sheet-like pulp, a superabsorbent polymer, and a heat-fusible fiber are mixed is placed in a predetermined form on the transported thin paper 12b. At that time, the absorbent-body material 12a is substantially rectangular, has a rear end that is curved in its middle portion in the width direction toward a front end of the absorbent-body material 12a, and is disposed such that a longitudinal direction thereof is in the transport direction.

When the thin paper 12b and the absorbent-body material 12a placed thereon are transported, air is sucked from below the transporting apparatus 4. Thus, the thin paper 12b and the absorbent-body material 12a are drawn toward the transporting apparatus 4.

A surface of the transporting apparatus 4 is bent such that the thin paper 12b wraps around the absorbent-body material 12a when the layered thin paper 12b and absorbent-body material 12a are transported. The thin paper 12b is guided along the bent surface of the transporting apparatus 4, so that the absorbent-body material 12a is wrapped in the thin paper 12b. In this embodiment, a side serving as the surface of the absorbent article 1 as a final product faces the transporting apparatus 4. Accordingly, when the absorbent-body material 12a is wrapped in the thin paper 12b, end sections of the thin paper 12b in the width direction (the direction that intersects the transport direction) are overlapped and adhere to each other above the absorbent-body material 12a, and the thin paper 12b is formed into a tube. At that time, the absorbent-body materials 12a are supplied to the transporting apparatus 4 at predetermined intervals, and the plurality of the absorbent-body materials 12a are successively arranged with a spacing therebetween in the tubular thin paper 12b.

Next, in order to integrate the thin paper 12b and the absorbent-body material 12a wrapped therein, embossing is performed in which the front end section and the rear end section in the transport direction, and the middle section in the width direction (the direction that intersects the transport direction) that is closer to the front end than the middle in the transport direction are compressed to form embossed patterns. As described above, embossing is performed by causing a product to pass through between two rollers (not shown) that are vertically opposed to each other. For example, protrusions are formed on a portion of a lower roller provided on a side close to the transporting apparatus 4, the portion that abuts against a region of the absorbent-body material 12a at which an embossed pattern is to be formed when the absorbent-body material 12a has been transported to that portion. A surface of an upper roller opposed to the lower roller is flat. The absorbent-body material 12a wrapped in the thin paper 12b passes through between the upper roller and the lower roller, so that the protrusions compress the thin paper 12b together with the absorbent-body material 12a. With compression by the protrusions, a plurality of embossed patterns are formed, and thus the thin paper 12b and the absorbent-body material 12a are integrated.

The thin paper 12b and the absorbent-body material 12a that have been integrated by formation of the embossed patterns are cut with a cutter or the like along an external shape of the absorbent-body material 12a. The thin paper 12b and the absorbent-body material 12a after the cutting are transported to a position on the transporting apparatus 4, at which the belt-like surface sheet 14 that has been wound in a roll is supplied with hot-melt adhesive applied to an upper face of the surface sheet 14. The integrated thin paper 12b and absorbent-body material 12a are transported to be placed on the surface sheet 14.

Groove-embossing is performed on the thin paper 12b and the absorbent-body material 12a that have been transported together with the surface sheet 14. In groove-embossing, in a similar manner as in the case of the above-described embossing, a product passes through between two rollers that are vertically opposed to each other and an embossed pattern is formed with protrusions provided on one of the rollers. With the groove-embossing, groove sections 18 (FIG. 5) are formed which is attached to the compressed section, and a plurality of deep concave sections 19 (FIG. 5) having a deeper bottom section than that of the groove sections 18 are formed in the groove sections 18 along the groove sections 18. At that time, the roller having the protrusions is heated to approximately 50 to 200° C. Thus, in the groove-embossing, compression and heating is performed simultaneously, and the heat facilitates adhering of a heat-fusible fiber contained in the absorbent-body material 12a. As a result thereof, the groove sections 18 and the deep concave sections 19 are formed that integrate the thin paper 12b and the absorbent-body material 12a, and the surface sheet 14. In this embodiment, along the longitudinal direction in the middle section in the width direction of the absorbent-body material 12a as shown in FIG. 11, a first groove section 18a in the form of an elongated circle is formed in almost the entire region in the longitudinal direction, together with a plurality of second groove sections 18b in the form of arcs so as to connect parallel straight lines of the first groove section 18a. At that time, a width between the straight grooves of the first groove section 18a is substantially the same as the width of the top absorbent body 20, and the plurality of deep concave sections 19 are formed in the groove sections 18a and 18b. Accordingly, one of the rollers has continuous protrusions for the grooves for forming the first groove section 18a and the second groove sections 18b, and protrusions for forming the plurality of deep concave sections 19 are formed with a spacing therebetween on peak sections of the protrusions for the grooves. The groove sections 18a and 18b that have been formed by the groove-embossing have a function to prevent the surface sheet 14 from moving upward away from the absorbent-body material 12a. In addition, the groove sections 18a and 18b have a function to suppress spreading of menstrual blood and the like by facilitating permeation into the highly compressed section when the menstrual blood and the like flow into the groove sections 18a and 18b, along with a function to facilitate three-dimensional bending in order to bring the product into closer contact with user's body when the product is worn.

Main Production Step S300

As shown in FIG. 12, the back face sheet 30 is supplied onto the base absorbent body 10 that has been produced in the base-absorbent-body production step S200. At that time, hot-melt adhesive has been applied to almost the entire face of the back face sheet 30, and the back face sheet 30 adheres to the base absorbent body 10. Herein, the back face sheet 30 is a belt-like sheet that is sufficiently wider than the base absorbent body 10.

When the base absorbent body 10 and the back face sheet 30 placed on the base absorbent body 10 are transported, round sealing is performed as a sheet-member joining step in which a joined section 31 is formed throughout the entire periphery of the outer edge in the shape of the absorbent article 1 viewed from above. At that time, the rear end side of the base absorbent body 10 curves in the middle in the width direction toward the front end side, and thus the round-sealed joined section 31 is formed wide on the rear side of the base absorbent body 10. Round sealing refers to a processing in which a portion that is along the external shape and is to be the outer edge in the shape of the absorbent article 1 viewed from above is heat-pressed and cured, but the heat-pressing does not have to be performed throughout the entire periphery. For example, it is acceptable that the rear end side of the base absorbent body 10 is joined along the outer edge of the absorbent-body material 12a, and a portion that is to be the outer edge of the produced absorbent article 1 is not joined thereto.

Round sealing is performed by causing a product to pass through between two rollers (not shown) that are vertically opposed to each other. For example, when the base absorbent body 10 and the back face sheet 30 under pressure and heat are caused to pass through between a patterned roller whose surface has protrusions matched to the outer edge in the shape of the absorbent article 1 viewed from above and a smooth roller whose surface is substantially smooth, the joined section 31 is formed that is substantially matched to the outer edge in the shape of the absorbent article 1 viewed from above. At that time, the heating temperature during the round sealing is set to a temperature at which the thermoplastic back face sheet 30 is not damaged.

When the base absorbent body 10 and the back face sheet 30 that have been joined into the external shape of the absorbent article 1 are transported, the continuous body 21 that has been produced in the continuous-body production step S100 is supplied from below the base absorbent body 10 onto the transporting apparatus 4. At that time, positioning is performed in such a manner as the absorbent-body material 12a of the top absorbent body 20 is in the middle in the width direction of the base absorbent body 10 and as an end section of the reinforced section 26 on the front side of the absorbent-body material 12a is at the front end of the base absorbent body 10. The top absorbent body 20 contained in the continuous body 21 is supplied such that a side of the top absorbent body 20 that abuts against user's body, that is, a side having the intermediate sheet 16 is opposed to the transporting apparatus 4. The continuous body 21 is supplied in a state where hot-melt adhesive has been applied to the reinforced section 26 on a side close to a front end 12f of each absorbent-body material 12a.

Next, embossing as a continuous-body joining step is performed on portions where the base absorbent body 10 overlaps the reinforced sections 26 and 25 on the respective sides close to the front end 12f and a rear end 12g in the absorbent-body material 12a of the continuous body 21. At that time, with the embossing of pressing almost the entire region of the reinforced section 26 on the side close to the front end 12f in the absorbent-body material 12a, the reinforced section 26 and the base absorbent body 10 are permanently joined to each other in an undetachable manner because an adhesive exists therebetween. The reinforced section 26 and the base absorbent body 10 can be permanently joined to each other even with a small pressure, by increasing the line diameter of the hot-melt adhesive that is applied to the reinforced section 26 of the continuous body 21 that is supplied at this stage. Furthermore, heat may be applied to the extent that the back face sheet 30 is not damaged. In this embodiment, in addition to the embossing of pressing almost the entire region of the reinforced section 26, embossing is partially performed on a position where the absorbent-body material 12a is not present on the front end side in the base absorbent body 10, and thus firmer permanent joining is realized.

On the other hand, the reinforced section 25 on a side close to the rear end 12g in the absorbent-body material 12a and the base absorbent body 10 are temporarily joined to each other in a detachable manner because no adhesive exists therebetween. Embossing for temporarily joining the reinforced section 25 and the base absorbent body 10 is performed on a position where the absorbent-body material 12a is not present, in the vicinity of a portion curved in the base absorbent body 10 toward the front end side on the rear end side of the base absorbent body 10. Accordingly, in the reinforced section 25 on the side close to the rear end 20b in the top absorbent body 20, the non-joined section 20c in which the reinforced section 25 and the base absorbent body 10 are not joined to each other is formed between the temporarily joined section 25c and the rear end 1b of the produced absorbent article 1. The non-joined section 20c is provided having a length that allows the non-joined section 20c to be held by a user of the absorbent article 1, and serves as the handle section. More specifically, with the embossing by which the reinforced section 25 and the base absorbent body 10 are temporarily joined, the portion on the rear end 20b side in the top absorbent body 20 is temporarily joined such that it can be detached and easily separated from the base absorbent body 10 without impairing the functions of the base absorbent body 10 and the top absorbent body 20, and the handle section 25a is formed in the rear end section of the top absorbent body 20. Regarding the embossing that temporarily joins the reinforced section 25 of the continuous body 21 and the base absorbent body 10 and the embossing that permanently joins the reinforced section 26 of the continuous body 21 and the base absorbent body 10, it is acceptable to perform either one of them in two steps one after another, or it is also acceptable to perform them in one step using an apparatus in which a single roller has protrusions for the front end and protrusions for the rear end. Furthermore, when permanently joining the reinforced section 26 on the front end 20a side in the top absorbent body 20 and the base absorbent body 10, embossing does not necessarily have to be performed. They can be permanently joined to each other in an undetachable manner only by compression-bonding, because hot-melt adhesive has been applied in advance to the reinforced section 26 on the front end 20a side. It should be noted that even in a case where the permanent joining and the temporary joining are performed in one step by compression-bonding, it is possible to temporarily join the reinforced section 25 and the base absorbent body 10 in a detachable manner because no adhesive exists between the reinforced section 25 and the base absorbent body 10.

Next, the release sheet 34 to which hot-melt adhesive has been applied is placed in the middle section of the back face sheet 30. More specifically, the adhesive 35 is not directly applied to the back face sheet 30, but supplied to the back face sheet 30 in a state where the adhesive 35 is applied to the release sheet 34. When the release sheet 34 is transferred onto the back face sheet 30 and then removed therefrom, the adhesive 35 remains on the back face sheet 30. Herein, the release sheet 34 may be joined to the base absorbent body 10 after being attached to the back face sheet 30.

After the release sheet 34 is placed on the back face sheet 30, cutting with a cutter or the like is performed along the outer edge in the shape of the absorbent article 1 viewed from above, in a state where the continuous body 21, the base absorbent body 10, the back face sheet 30, and the like superpose. At that time, the cutting is performed at the joined section 31 that has been joined by round sealing. Furthermore, the continuous body 21 is cut at the positions where the front end 20a and the rear end 20b of the top absorbent body 20 being formed are matched to the front end and the rear end of the back face sheet 30.

In this embodiment, an example was described in which round sealing is performed throughout the entire periphery of the outer edge in the shape of the absorbent article 1 viewed from above. When the base absorbent body, top absorbent body, and the like that are transported are cut with a cutter in which a blade is provided on the surface of a roller, it is desirable that round sealing is performed at least on the front end and the rear end in the transport direction in the outer edge in the shape of the absorbent article 1 viewed from above. When round sealing is performed on the front end and the rear end in the transport direction, the front end and the rear end are hardened and can be easily cut. This makes it possible to prevent the base absorbent body 10 and the like after the cutting from being attached to the roller having the cutter blade, and to separate the base absorbent body 10 and the like from the cutter in such a manner as to move the base absorbent body 10 and the like in the transport direction.

Wrapping Preparation Step S400 (FIG. 13)

When each absorbent article 1 that has been produced in the main production step S300 passes through between bent walls (not shown) arranged above the transporting apparatus 4, the holding sections 32 are guided along the walls and bent toward the surface side. The release sheet 34 to which the hot-melt adhesives 35 have been applied is placed from the transporting apparatus 4 onto the bent holding sections 32. The absorbent article 1 in this state is folded into a substantially rectangular shape.

The orientation of the absorbent article 1 on which the release sheet 34 has been placed is changed such that the longitudinal direction is perpendicular to the transport direction. Then, the absorbent article 1 is supplied to the wrapping step S500.

Wrapping Step S500

As shown in FIG. 14, the belt-like wrapping sheet 36 is supplied onto the transporting apparatus 4. On the wrapping sheet 36, the absorbent article 1 subjected to the wrapping preparation is placed with the surface side up. At that time, the absorbent article 1 whose surface side was facing the transporting apparatus 4 until before the wrapping preparation step S400 is turned upside down and placed with the surface side up. A trace amount of hot-melt adhesive has been applied to several positions in the wrapping sheet 36 in the longitudinal direction of the absorbent article 1, and thus the back face side of the absorbent article 1 adheres to the wrapping sheet 36 at the several positions.

When the absorbent article 1 placed on the wrapping sheet 36 passes through between bent wall sections (not shown) arranged separately from and above the transporting apparatus 4, the absorbent article 1 and the wrapping sheet 36 are guided along the wall sections and folded in three such that the absorbent article 1 is wrapped. When the wrapping sheet 36 is bent together with the absorbent article 1, the rear end 36b of the wrapping sheet 36 adheres to the surface side in the absorbent article 1 via an adhesive that has been applied to the rear end 36b of the wrapping sheet 36. On the wrapping sheet 36 on a side close to the bent rear end 36b, the absorbent article 1 is bent together with the wrapping sheet 36 on a side close to the front end 36a, the front end 36a of the wrapping sheet 36 is overlapped on an outer face of the wrapping sheet 36 that has been already bent and is fixed by the tape 38. With this bending operation, a plurality of the absorbent articles 1 bent in the tubular wrapping sheet 36 are arranged and transported with a spacing therebetween in the transport direction.

Subsequently, when portions between the adjacent absorbent articles 1 are compression-joined during the transportation, the absorbent articles 1 are obtained that are connected in an individually wrapped state. Finally, the centers of the compression-joined portions between the absorbent articles 1 are cut with a cutter or the like, and thus the individually wrapped absorbent articles 1 are completed.

With the method for producing the absorbent article 1 according to the first embodiment, cutting is performed along the external shape of the absorbent article 1 after the base absorbent body 10, the back face sheet 30, and the continuous body 21 are joined to each other. Thus, the absorbent article 1 can be produced by cutting all of the base absorbent body 10, the back face sheet 30, and the continuous body 21 in one cutting step. At that time, the cutting is performed at a portion that defines the external shape of the absorbent article 1 in which the base absorbent body 10 and the back face sheet 30 have been joined to each other in the sheet-member joining step. Thus, it is possible to produce a tough absorbent article 1 in which an external edge section of the formed absorbent article 1 is joined. Moreover, in one top absorbent body 20 obtained by cutting the continuous body 21, the reinforced section 26 in the front end 20a is permanently joined in an undetachable manner, and the reinforced section 25 in the rear end 20b is temporarily joined in a detachable manner. Thus, the reinforced section 25 in the rear end 20b can be detached from the base absorbent body 10, and the top absorbent body 20 can be joined to the base absorbent body 10 only at the reinforced section 26 in the front end 20a. That is to say, it is possible to produce the absorbent article 1 that can be used in a state where the portion on the rear end 20b side is separated from the base absorbent body 10. Accordingly, for example, it is possible to produce the absorbent article 1 in which the top absorbent body 20 can be separated from the base absorbent body 10 and placed in the groove between the buttocks to be in close contact with user's body in use. Moreover, the reinforced section 25 on the rear end 20b side in the top absorbent body 20 is temporarily fixed inside the joined section 31 that has been joined in the sheet-member joining step. Thus, a portion from the temporarily joined section to the rear end 20b in the top absorbent body 20 is not joined to the base absorbent body 10. Accordingly, it is possible to produce the absorbent article 1 in which the top absorbent body 20 and the base absorbent body 20 can be easily detached from each other by holding the rear end 20b of the top absorbent body 10.

Furthermore, the reinforced section 26 in the front end 20a in the longitudinal direction of one top absorbent body 20 contained in the continuous body 21 and the base absorbent body 10 are compression-bonded via an adhesive. Thus, it is possible to more firmly join the reinforced section 26 in the front end 20a in the longitudinal direction of one top absorbent body 20 contained in the continuous body 21 and the base absorbent body 10 such that they cannot be detached from each other.

Second Embodiment

With the production method according to the first embodiment, the absorbent article 1 is produced by joining the continuous body 21 in which the top absorbent bodies 20 are continuously arranged and the base absorbent body 10. With the production method according to the second embodiment, a single top absorbent body 20 is produced in advance, and the single top absorbent body 20 and the base absorbent body 10 are joined to each other. In the following description, the same elements as in the first embodiment are given the same reference numerals, and a description thereof and similar steps is omitted.

The method for producing the absorbent article according to the second embodiment is different from the production method according to the first embodiment; the difference is in that the continuous body 21 is cut into individual top absorbent bodies 20 after the continuous-body production step S100, and that the continuous body 21 is not cut in the main production step S300. Accordingly, in the second embodiment, a continuous-body cutting step S150 of cutting the continuous body 21 is added after the continuous-body production step S100 of the first embodiment, and these steps serve as a single-absorbent-body production step S110. A main production step S301 is performed in which the step of cutting the continuous body 21 has been excluded from the main production step S300 of the first embodiment.

Figure 15:
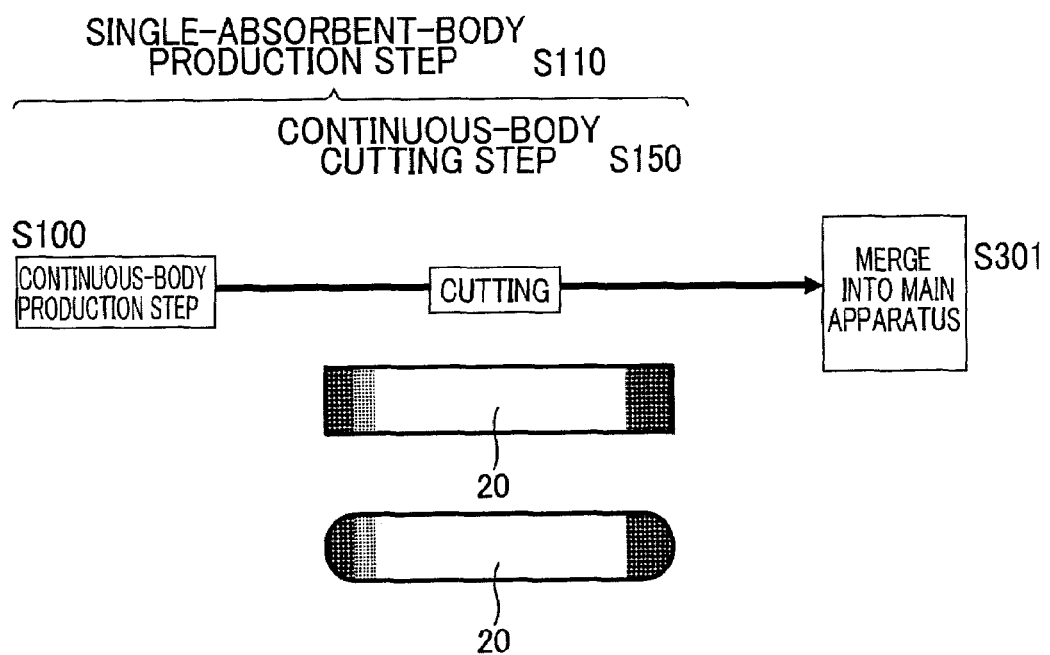
FIG. 15 is a diagram for illustrating a continuous-body cutting step.
Figure 16:
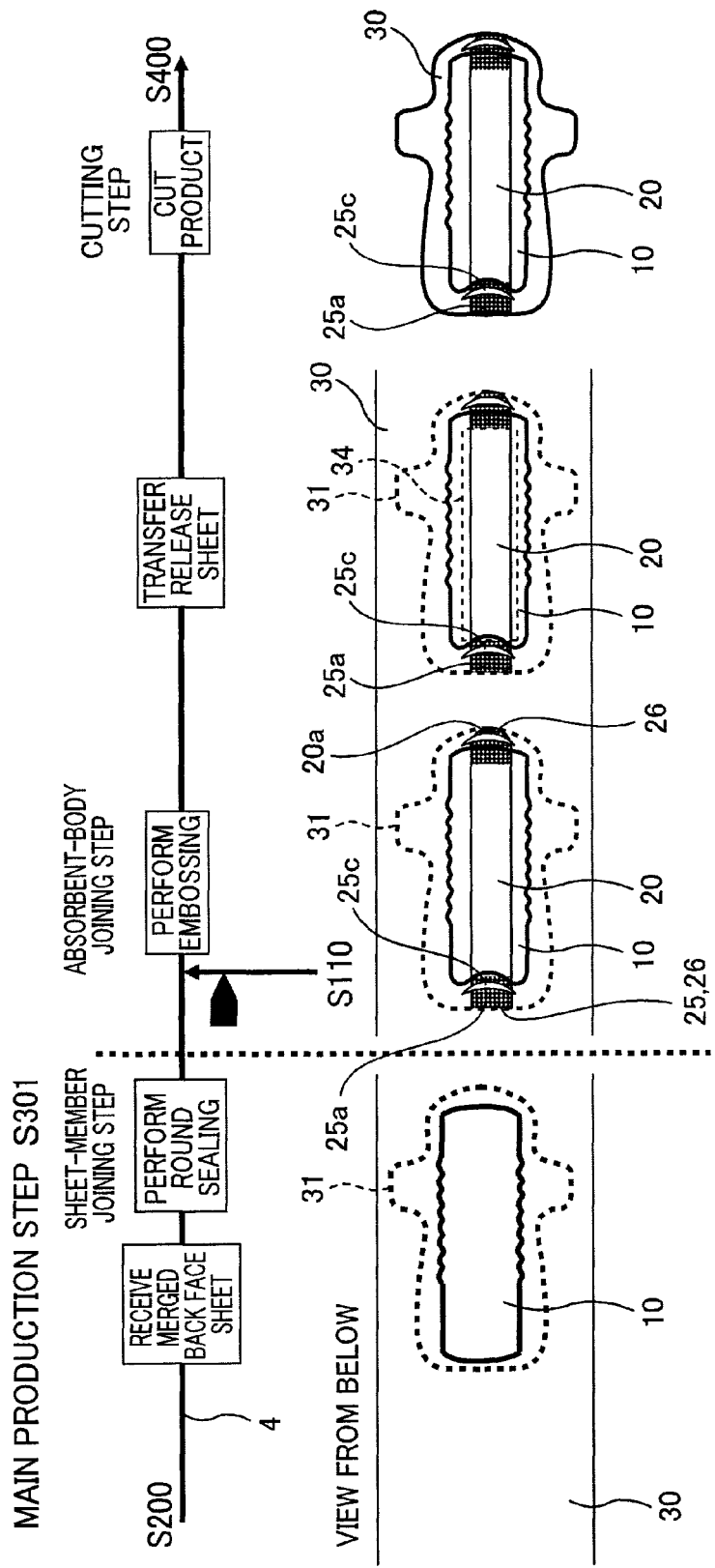
FIG. 16 is a diagram for illustrating a main production step of a second embodiment.

FIG. 15 is a diagram for illustrating the continuous-body cutting step. FIG. 16 is a diagram for illustrating the main production step of the second embodiment.

Single-Absorbent-Body Production Step S110 As shown in FIG. 15, with the method for producing the absorbent article according to the second embodiment, the continuous body 21 that has been produced in the continuous-body production step S100 is cut in the continuous-body cutting step S150 into single top absorbent bodies 20 with a cutter or the like at the reinforced sections 25 and 26 on which embossing has been performed. At that time, the top absorbent body 20 is cut such a length as the rear end 20b substantially matches the rear end of the back face sheet 30 when the top absorbent body 20 is joined to the base absorbent body 10. The top absorbent body 20 after the cutting is supplied to the main production step S301.

Main Production Step S301

As shown in FIG. 16, when the back face sheet 30 is supplied onto the base absorbent body 10 that has been produced in the base-absorbent-body production step S200, round sealing is performed as a sheet-member joining step throughout an entire periphery of the outer edge in the shape of the absorbent article 1 viewed from above, and thus the joined section 31 is formed.

When the base absorbent body 10 and the back face sheet 30 are transported on which round sealing has been performed along the external shape of the absorbent article 1, the single top absorbent body 20 that has been produced in the single-absorbent-body production step S110 is supplied from below the base absorbent body 10 onto the transporting apparatus 4. At that time, positioning is performed in such a manner as the top absorbent body 20 is in the middle in the width direction of the base absorbent body 10 and as the reinforced section 26 on a side close to the front end 20a in top absorbent body 20 is at the front end of the base absorbent body 10. At that time, the rear end 20b of the top absorbent body 20 is disposed in such a manner as the rear end 20b substantially matches the rear end of the back face sheet 30. The top absorbent body 20 is supplied in a state where hot-melt adhesive has been applied to the reinforced section 26 on the side close to the front end 20a.

Next, embossing as an absorbent-body joining step is performed on portions where the base absorbent body 10 overlaps the reinforced sections 26 and 25 on the respective sides close to the front end 20a and the rear end 20b in the top absorbent body 20. At that time, with the embossing of pressing almost the entire region of the reinforced section 26, the reinforced section 26 of the top absorbent body 20 and the base absorbent body 10 are permanently joined to each other in an undetachable manner because an adhesive exists therebetween. The reinforced section 26 and the base absorbent body 10 can be permanently joined to each other even with a small pressure, by increasing the line diameter of the hot-melt adhesive that is applied to the reinforced section 26 of the top absorbent body 20 that is supplied at this stage. Furthermore, heat may be applied to the extent that the backface sheet 30 is not damaged In this embodiment, in addition to the embossing of pressing almost the entire region of the reinforced section 26, embossing is partially performed on the position where the absorbent-body material 12a is not present on the front end side in the base absorbent body 10, and thus firmer permanent joining is realized. On the other hand, the reinforced section 25 of the top absorbent body 20 and the base absorbent body 10 are temporarily fixed to each other in a detachable manner because no adhesive exists therebetween. Embossing for temporarily joining the reinforced section 25 and the base absorbent body 10 is performed on the position where the absorbent-body material 12a is not present, in the vicinity of the portion curved toward the front end side on the rear end side in the base absorbent body 10. Accordingly, in the reinforced section 25 on the side of the rear end 20b in the top absorbent body 20, the non-joined section 20c in which the reinforced section 25 and the base absorbent body 10 are not joined to each other is formed between the temporarily joined section 25c and the rear edge 1b of the produced absorbent article 1. The non-joined section 20c is set to have a length in such a manner as the user of the absorbent article 1 can hold it, and serves as the handle section 25a. More specifically, with the embossing of temporarily joining the reinforced section 25 and the base absorbent body 10, the portion on the side of the rear end 20b in the top absorbent body 20 is temporarily joined to the extent that it can be detached and easily separated from the base absorbent body 10 without impairing the function of the base absorbent body 10 and the top absorbent body 20, and the handle section 25a is formed in the rear end section of the top absorbent body 20. The embossing of temporarily joining the reinforced section 25 of the top absorbent body 20 and the base absorbent body 10 and the embossing of permanently joining the reinforced section 26 of the top absorbent body 20 and the base absorbent body 10 may be performed in two steps one after another, or may be performed in one step using an apparatus in which one roller has protrusions for the front end and protrusions for the rear end. Furthermore, when permanently joining the reinforced section 26 on the side of the front end 20a in the top absorbent body 20 and the base absorbent body 10, embossing does not necessarily have to be performed. The reinforced section 26 and the base absorbent body 10 can be permanently joined to each other in an undetachable manner only by compression-bonding, because hot-melt adhesive has been applied in advance to the reinforced section 26 on the side of the front end 20a. It should be noted that even in a case where the permanent joining and the temporary joining are performed in one step by compression-bonding, the reinforced section 25 and the base absorbent body 10 can be temporarily joined to each other in a detachable manner because no adhesive exists between the reinforced section 25 and the base absorbent body 10.

Next, the release sheet 34 to which hot-melt adhesive has been applied is placed in the middle section of the back face sheet 30.

After the release sheet 34 is placed on the back face sheet 30, cutting with a cutter or the like is performed along the outer edge in the shape of the absorbent article 1 viewed from above, that is, along the joined section 31 that has been joined by round sealing, in a state where the top absorbent body 20, the base absorbent body 10, the back face sheet 30, and the like superpose. The individual absorbent article 1 obtained by the cutting with a cutter or the like is supplied to the wrapping preparation step S400.

With the method for producing the absorbent article 1 according to the second embodiment, after the base absorbent body 10 and the back face sheet 30 are joined to each other, cutting is performed along the external shape of the absorbent article 1. Thus, the absorbent article 1 can be produced by cutting both of the base absorbent body 10 and the back face sheet 30 in a single cutting step. At that time, the absorbent article 1 is cut at the joined section 31 that defines the external shape of the absorbent article 1 in which the base absorbent body 10 and the back face sheet 30 have been joined to each other in the sheet-member joining step. Thus, the external edge section of the formed absorbent article 1 is joined so that a tough absorbent article 1 can be produced. Moreover, in the top absorbent body 20, the reinforced section 26 in the front end 20a is permanently joined in an undetachable manner, and the reinforced section 25 in the rear end 20b is temporarily joined in a detachable manner. Thus, it is possible to join the top absorbent body 20 and the base absorbent body 10 only at the reinforced section 26 in the front end 20a with the reinforced section 25 in the rear end 20b being detached from the base absorbent body 10. That is to say, it is possible to produce the absorbent article 1 that can be used in a state where the reinforced section 25 on the rear end 20b side is separated from the base absorbent body 10. Accordingly, for example, it is possible to produce the absorbent article 1 that can be used in close contact with user's body by separating the top absorbent body 20 from the base absorbent body 10 and placing the top absorbent body 20 in the groove between the buttocks. Moreover, the reinforced section 25 in the rear end 20b in the top absorbent body 20 is temporarily fixed inside the joined section 31 that has been joined in the sheet-member joining step. Thus, the portion from the temporarily joined section 25c to the rear end 20b in the top absorbent body 20 is not joined to the base absorbent body 10. Accordingly, it is possible to produce the absorbent article 1 in which the top absorbent body 20 and the base absorbent body 10 can be easily detached from each other by holding a portion from the temporarily joined section 25c to the rear end 20b in the top absorbent body 20. The reinforced section 26 in the front end 20a in the longitudinal direction of the top absorbent body 20 and the base absorbent body 10 are compression-bonded via an adhesive. Thus, the reinforced section 26 in the front end 20a in the longitudinal direction of the top absorbent body 20 and the base absorbent body 10 can be more firmly joined to each other such that they cannot be detached from each other.

Furthermore, since the top absorbent body 20 is produced as a single member in the single-absorbent-body production step S110, the length of the top absorbent body 20 can be freely set. Accordingly, with a single production method, it is possible to produce various absorbent articles 1 that have top absorbent bodies 20 having various lengths.

Furthermore, with the method for producing the absorbent article 1 according to the first and second embodiments, it is possible to produce the absorbent article 1 in which the top absorbent body 20 and the base absorbent body can be easily detached from each other by holding the handle section 25a that is formed without being projected from the outer edge of the absorbent article 1. Accordingly, it is possible to reduce the size of the absorbent article 1 that can be easily worn. Thus, it is possible to provide the absorbent article 1 having more excellent portability. Furthermore, since the back face of the base absorbent body 10 and the back face sheet 30 are heat-pressed via an adhesive, the base absorbent body 10 and the back face sheet 30 can be more firmly joined to each other at a portion that defines the outer edge of the absorbent article 1, and thus a tougher absorbent article 1 can be produced.

Moreover, since a portion that is permanently joined in an undetachable manner in the top absorbent body 10 is the reinforced section 26 that has been reinforced, it is possible to produce the absorbent article 1 in which the top absorbent body 20 is unlikely to be damaged even when a section that has been firmly joined is pulled. Furthermore, since a portion that is temporarily joined in a detachable manner in the top absorbent body 20 is the reinforced section 25 that has been reinforced, it is possible to produce the absorbent article 1 in which the top absorbent body 20 is unlikely to be damaged even when the temporarily joined section 25c is detached.

In the absorbent article 1 produced with the method for producing the absorbent article 1 according to the first and second embodiments, the front end 20a of the top absorbent body 20 is permanently joined, and the rear end 20b is temporarily joined. Thus, it is possible to join the top absorbent body 20 and the base absorbent body 10 only at the front end 20a with the rear end 20b being detached from the base absorbent body 10. Thus, it is possible to use the absorbent article 1 in a state where the portion on the rear end 20b side is separated from the base absorbent body 10. Accordingly, it is possible to realize the absorbent article 1 that can be used in close contact with user's body by separating the top absorbent body 20 from the base absorbent body 10 and placing the top absorbent body 20 in the groove between the buttocks. In particular, the reinforced section 25 in the rear end 20b in the top absorbent body 20 is temporarily fixed inside the joined section 31 that has been joined in the sheet-member joining step. Thus, a portion from the rear end 20b to the temporarily joined section 25c in the top absorbent body 20 can serve as the handle section 25a that is not joined to the base absorbent body 10. Accordingly, it is possible to realize the absorbent article 1 in which the top absorbent body 20 and the base absorbent body can be easily detached from each other by holding the handle section 25a at the edge side of the rear end 20b of the top absorbent body 20, the handle section 25a being formed without being projected from the base absorbent body 10 or the like. Accordingly, it is possible to reduce the size of the absorbent article 1 that can be easily worn. Thus, it is possible to provide the absorbent article 1 having excellent portability.

Figure 17:
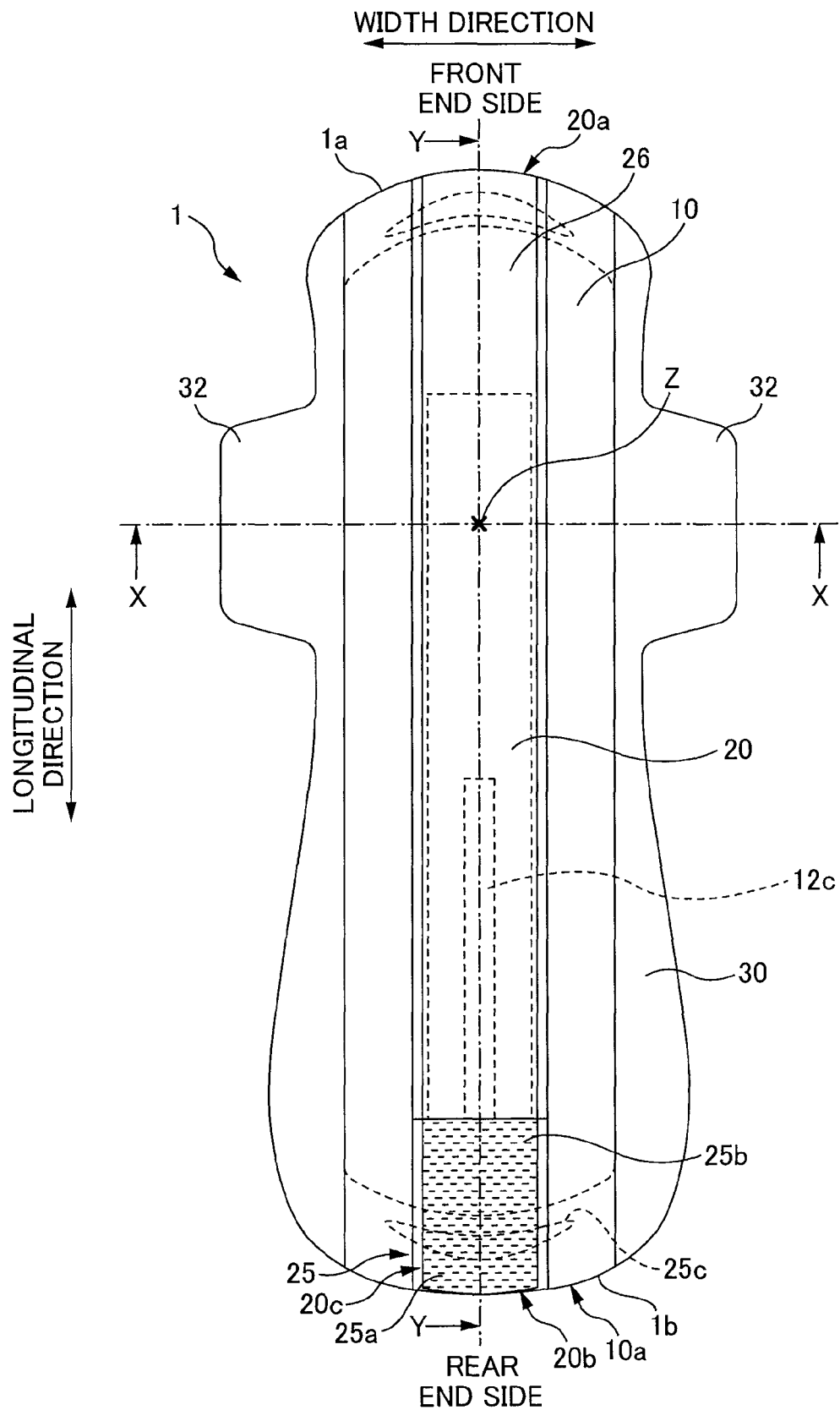
FIG. 17 is a view showing a modified example of the absorbent article according to the first and second embodiments.

FIG. 17 is a view showing a modified example of the absorbent article according to the first and second embodiments. In the foregoing embodiments, an example was described in which the absorbent-body material 12a is curved on the rear end side in the base absorbent body 10 toward the front portion, and the temporarily joined section 25c is disposed inside the absorbent article 1. However, a configuration is also possible in which the absorbent-body material 12a of the base absorbent body 10 is shortened, and the vicinity of the rear end of the absorbent-body material 12a is temporarily joined, and thus the temporarily joined section 25c is disposed on the inner side of the rear end 1b in the absorbent article 1, as shown in FIG. 17.

Third Embodiment

In the absorbent article 1 according to the foregoing first and second embodiments, the base absorbent body 10 as an absorbent-article main body included the absorbent-body base material 12 and the surface sheet 14. However, the absorbent-article main body does not have to include the absorbent-body base material 12.

Hereinafter, an example of an absorbent article 2 according to the third embodiment will be described in which the absorbent-article main body is constituted only by the surface sheet 14. In the following description, the same elements as in the first embodiment are given the same reference numerals, and a description thereof and similar steps are omitted.

Figure 18:
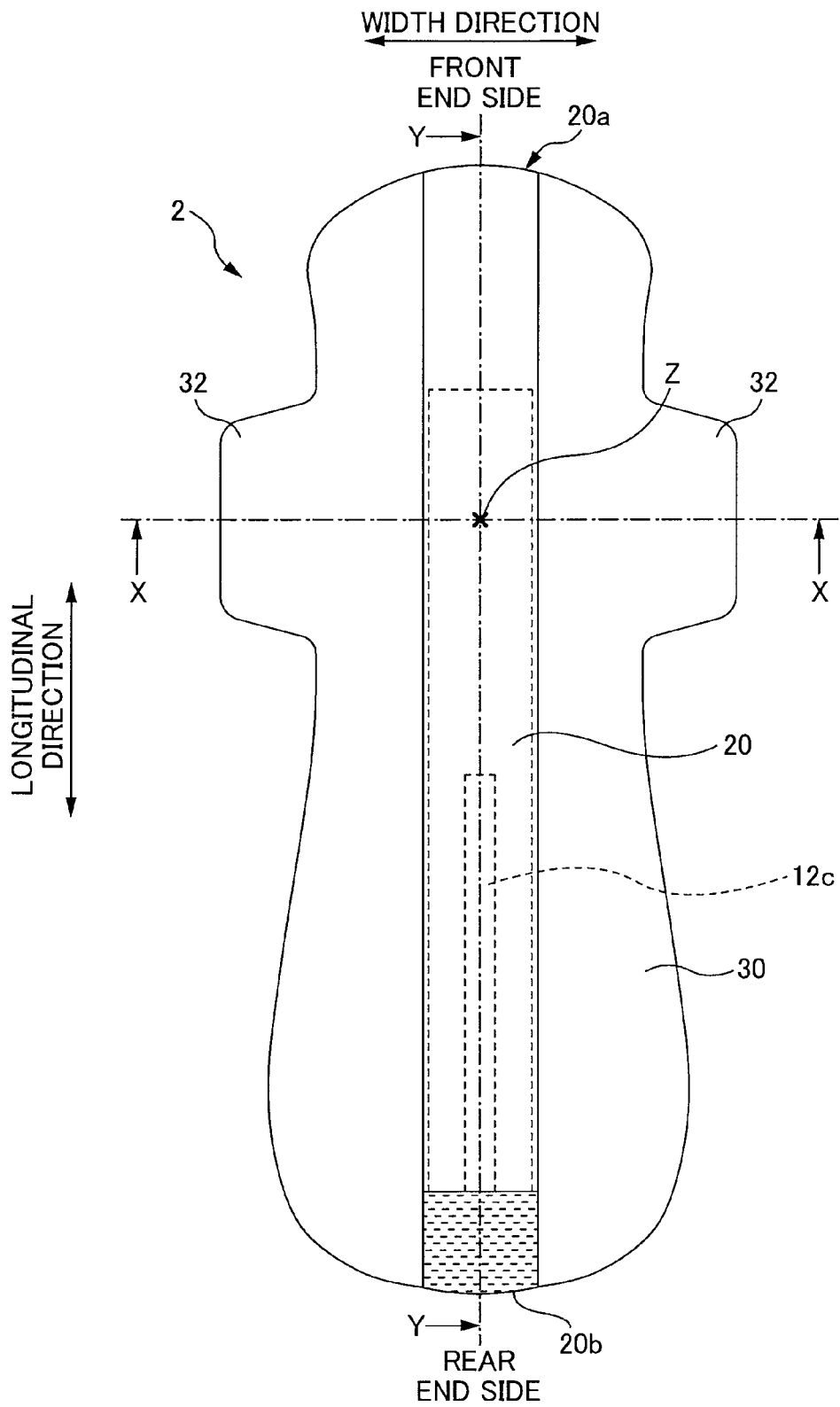
FIG. 18 is a plan view showing a surface side of an absorbent article according to a third embodiment.

FIG. 18 is a plan view showing the surface side of an absorbent article according to the fourth embodiment. As shown in the figure, the absorbent article 2 in the third embodiment is elongated in a predetermined direction. The absorbent article 2 includes the surface sheet 14 that is an absorbent-article main body, the back face sheet 30 that is a sheet member provided on a back face side as one face of the surface sheet 14 and is for preventing fluid that is to be absorbed by the top absorbent body 20 from leaking to the back face side, and the top absorbent body 20 that is an absorbent body joined to a surface as another face of the surface sheet 14 and disposed along the longitudinal direction in the middle in the width direction of the surface sheet 14.

The top absorbent body 20 is disposed on the surface sheet 14 in its longitudinal direction. On the sides respectively close to the front end 20a and the rear end 20b of the top absorbent body 20, the reinforced sections 25 and 26 are formed. The reinforced section 26 on the side close to the front end 20a as one end section of the top absorbent body 20 is permanently joined to the surface sheet 14, and the reinforced section 25 on the side close to the rear end 20b as the other end section is formed such that the reinforced section 25 can be separate from the surface sheet 14. Before use, the reinforced section 25 on the rear end 20b side is temporarily joined at a position where a portion that is not joined to the absorbent-article main body is formed and that is closer to the rear end than the temporarily joined section 25c formed by embossing so as to be held by a user of the absorbent article, inside the joined section 31 in which the surface sheet 14 and the back face sheet 30 are joined at the outer edge section.

In the third embodiment, an example was described in which the absorbent-article main body is constituted simply by the surface sheet 14. However, the absorbent-article main body may include a member formed by layering a sheet-like member in addition to the surface sheet 14.

Method for Producing Absorbent Article of Third Embodiment

Figure 19:
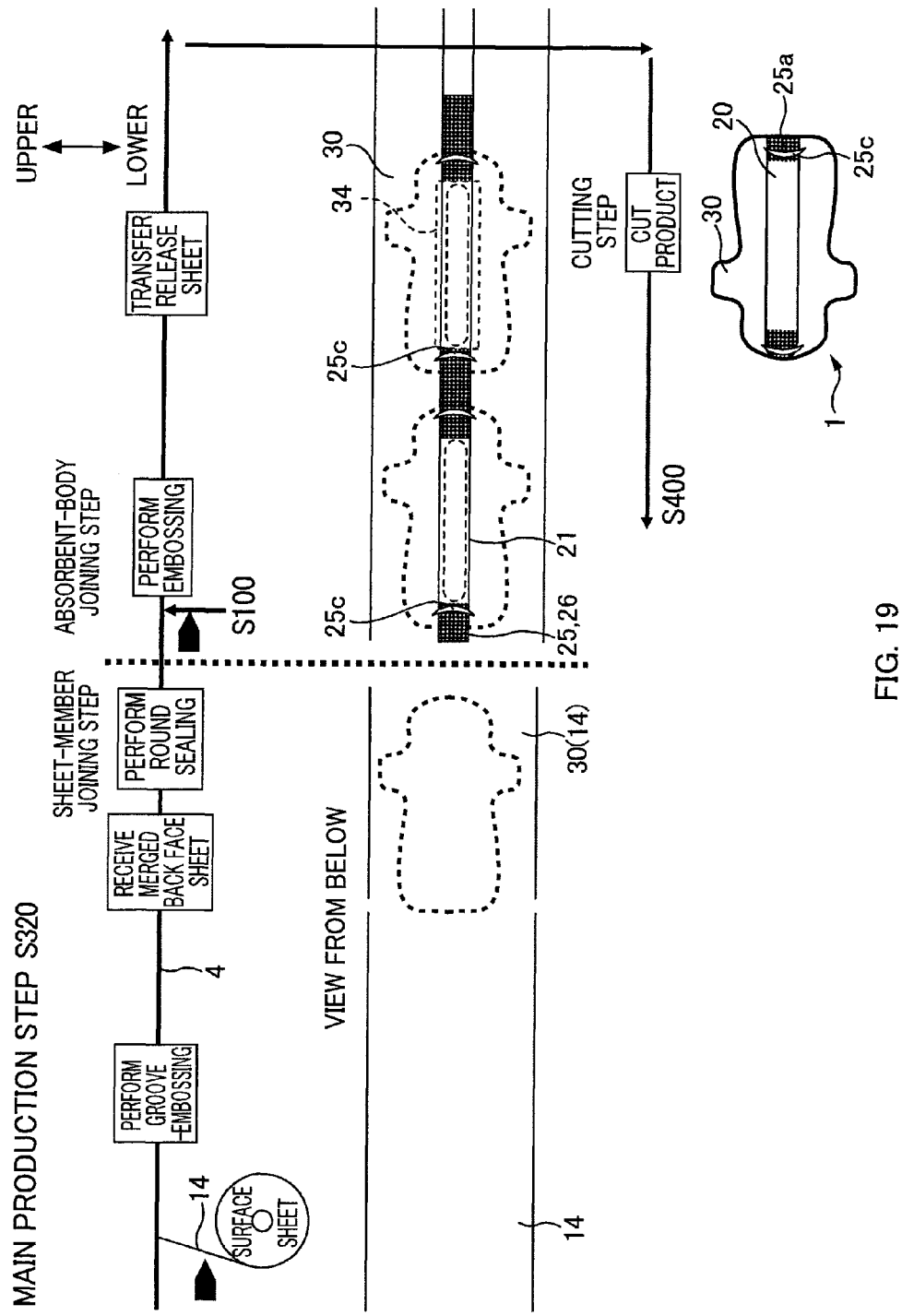
FIG. 19 is a diagram for illustrating a main production step of the third embodiment.

Hereinafter, a method for producing the absorbent article 2 according to the third embodiment will be described. FIG. 19 is a diagram for illustrating a main production step of the third embodiment.

In the absorbent article 2 according to the third embodiment, the top absorbent body 20 may be produced as the continuous body 21, or may be produced as a single absorbent body. In this example, a method for producing the top absorbent body 20 as the continuous body 21 will be described. The method for producing the absorbent article 2 includes the continuous-body production step S100, a main production step S320, the wrapping preparation step S400, and the wrapping step S500. This method is different from the production method according to the first embodiment, in that there is no step corresponding to the base-absorbent-body production step in the foregoing embodiments because the absorbent-article main body is constituted only by the surface sheet 14, and the surface sheet 14 is supplied initially in the main production step S320.

Main Production Step S320

As shown in FIG. 19, the belt-like surface sheet 14 as an absorbent-article main body is supplied onto the transporting apparatus 4. In the transporting apparatus 4, the back face sheet 30 is supplied onto the surface sheet 14 that is being transported. When the surface sheet 14 and the back face sheet 30 placed thereon are transported, round sealing is performed as a sheet-member joining step of forming the joined section 31 throughout the entire outer edge of the shape of the absorbent article 2 viewed from above, and a portion that is to be the outer edge is hardened by heat-pressing throughout the entire periphery. When the surface sheet 14 and the back face sheet 30 that are subjected to round sealing are transported, the continuous body 21 that has been produced in the continuous-body production step S100 is supplied from below the surface sheet 14 onto the transporting apparatus 4. At that time, the continuous body 21 is supplied such that a face of the continuous body 21 that abuts against user's body is opposed to the transporting apparatus 4, that is, a side on which the intermediate sheet 16 is provided is opposed to the transporting apparatus 4. The continuous body 21 is supplied in a state where hot-melt adhesive has been applied to the reinforced section 26 that is positioned on the front end side with respect to each absorbent-body material 12a.

Next, embossing as a continuous-body joining step is performed on portions where the surface sheet 14 overlaps the reinforced sections 25 and 26 on the respective sides close to the front end 12f and the rear end 12g in the absorbent-body material 12a of the continuous body 21. At that time, the reinforced section 26 on the side close to the front end 12f in the absorbent-body material 12a and the surface sheet 14 are permanently joined to each other in an undetachable manner because an adhesive exists therebetween. On the other hand, the reinforced section 25 on the side close to the rear end 12g in the absorbent-body material 12a and the surface sheet 14 are temporarily fixed to each other in a detachable manner because no adhesive exists therebetween.

Furthermore, the embossing for temporarily fixing the reinforced section 25 and the surface sheet 14 is performed at a position where the reinforced section 25 that is not joined to the surface sheet 14 is formed, and that is closer to the rear end than the temporarily joined section formed by embossing so as to be held by a user of the absorbent article 2, inside the joined section 31 where the surface sheet 14 and the back face sheet 30 is subjected to round sealing. More specifically, with the embossing of temporarily joining the reinforced section 25 on the rear end 12g side and the surface sheet 14, the portion on the rear end 20b side in the top absorbent body 20 is joined in such a manner as to be allowed to split and easily separate from the base absorbent body 10 without impairing the function of the surface sheet 14 and the top absorbent body 20, and the handle section 25a is formed in the rear end section of the top absorbent body 20.

Next, the release sheet 34 to which hot-melt adhesive has been applied is placed on the back face sheet 30.

After the release sheet 34 is placed on the back face sheet 30, cutting with a cutter or the like is performed (cutting step) along the outer edge in the shape of the absorbent article 2 viewed from above, that is, along the joined section 31 that has been joined by round sealing, in a state where the continuous body 21, the surface sheet 14, the back face sheet 30, and the like superpose. At that time, the continuous body 21 is cut at the positions where the front end 20a and the rear end 20b of the top absorbent body 20 being formed are matched to the front end and the rear end of the back face sheet 30.

The individual absorbent article 2 obtained by the cutting with a cutter or the like is supplied to the wrapping preparation step S400.

With the method for producing the absorbent article according to the third embodiment, it is possible to easily produce a thin and compact absorbent article 2 in which the absorbent-article main body is constituted by the surface sheet 14.

Modified Example of Top Absorbent Body

In the foregoing embodiments, in the top absorbent body 20, the exterior of the absorbent-body material 12a and the intermediate sheet 16 is wrapped in the surface sheet 14, and the reinforced sections 25 and 26 are formed on the sides respectively close to the front end 20a and the rear end 20b of the top absorbent body 20 by performing embossing in a state where only the surface sheet 14 is folded and caused to adhere. However, in the top absorbent body 20, the absorbent-body material 12a may be present also in the reinforced sections 25 and 26.

Continuous-Body Production Step S120

Figure 20:
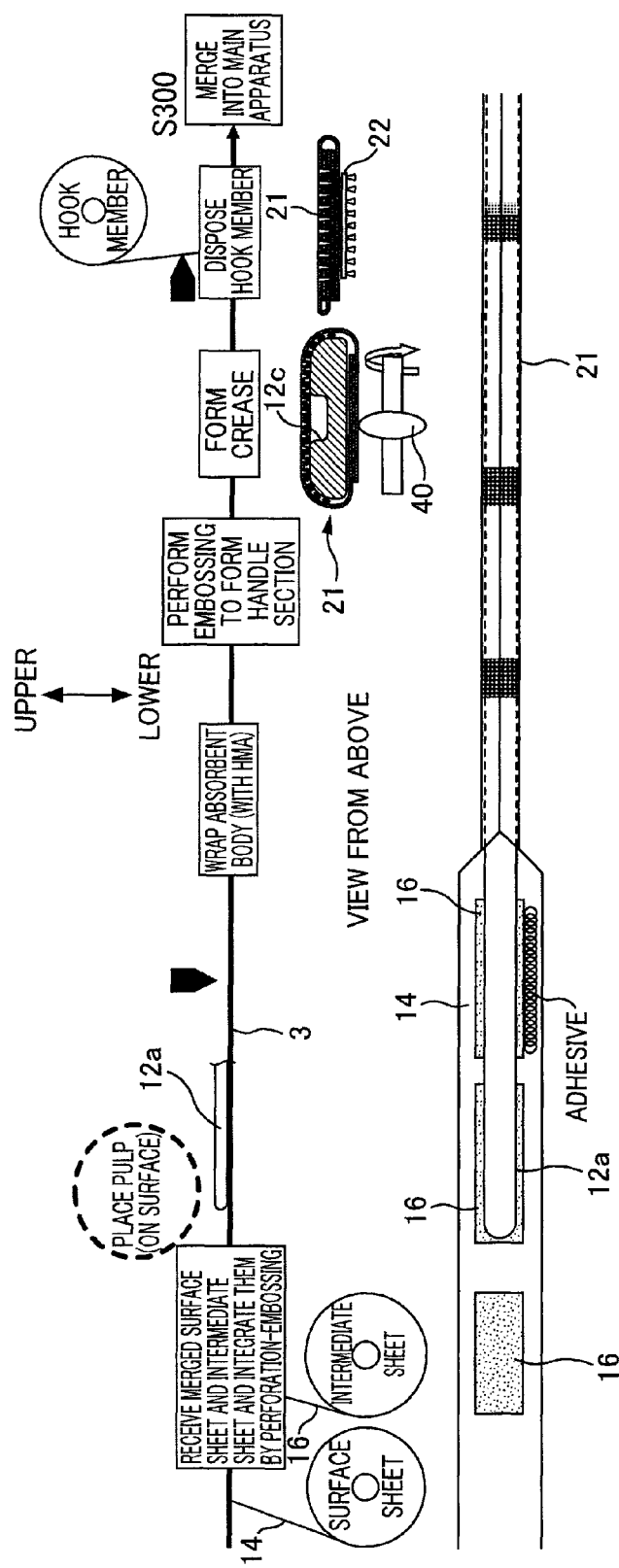
FIG. 20 is a diagram showing a method for producing a top absorbent body in which an absorbent-body material is present also in reinforced sections.

FIG. 20 is a diagram showing a method for producing a top absorbent body in which the absorbent-body material is present also in the reinforced sections.

The belt-like surface sheet 14 is supplied onto the transporting apparatus 3 for producing a continuous body.

The intermediate sheet 16 that has been cut in the form of a single sheet is supplied onto the transported surface sheet 14, and the surface sheet 14 and the intermediate sheet 16 are integrated by perforation-embossing.

When the surface sheet 14 and the intermediate sheet 16 that have been integrated are transported, a material in the form of a sheet such as airlaid pulp sheet or fluid-absorbent nonwoven fabric is placed as the absorbent-body material 12a on the intermediate sheet 16.

A hot-melt adhesive is applied to the surface sheet 14 at a position in the direction that intersects the transport direction of the absorbent-body materials 12a transported in one piece.

When the surface sheet 14 is guided along the bent surface of the transporting apparatus 3, the absorbent-body material 12a is wrapped in the surface sheet 14 that is integrated with the intermediate sheet 16.

Next, embossing is performed at predetermined intervals on the absorbent-body materials 12a that are formed in one piece and wrapped in the surface sheet 14. With this embossing, embossed patterns are formed, and the absorbent-body materials 12a are caused to adhere. In this case, a lower roller is used that has protrusions projected more than in the embossing performed on portions between the absorbent-body materials 12a adjacent to each other in the transport direction in the first embodiment. The protrusions compress the surface sheet 14, the absorbent-body material 12a, and the intermediate sheet 16. The compressed sections serve as the reinforced sections 25 and 26. Thus, the continuous body 21 of the top absorbent bodies 20 is produced in which the reinforced sections 25 and 26 are formed respectively at the front and rear of each absorbent-body material 12a.

The continuous body 21 is further transported, and a crease is formed along the thin wall section 12c of the absorbent-body material 12a.

Subsequently, the hook member 22 is supplied to a portion that is to serve as each of the top absorbent bodies 20 of the continuous body 21. The continuous body 21 is supplied to the main production step S300.

Other Embodiments

In the foregoing embodiments, for the sake of description, a configuration is described in which the base absorbent body 10 has one absorbent-body base material 12 in the middle in the width direction, but there is no limitation to this. For example, a configuration is acceptable in which both end sections of the base absorbent body 10 in the width direction each have a side absorbent body in the longitudinal direction. Further, a configuration is acceptable in which the both end sections each have a solid gather instead of the side absorbent body.

Furthermore, in the foregoing embodiments, an example is described in which the hook member 22 is provided on the rear end side in the top absorbent body 20, the hook member 22 being for fixing the top absorbent body 20 in a state where the position of the top absorbent body 20 has been adjusted in such a manner as to be in close contact with the bodily groove when the absorbent article 1 is worn. However, a member such as the hook member 22 for fixing the top absorbent body 20 does not necessarily have to be provided. In this case, the top absorbent body 20 is placed in the bodily groove, and thus the top absorbent body 20 is sandwiched and held in the bodily groove.

The foregoing embodiments are for the purpose of elucidating the understanding of the invention and are not to be interpreted as limiting the invention. The invention can of course be altered and improved without departing from the gist thereof, and any equivalents thereof are included in the scope of the invention.

The invention claimed is:

1. An absorbent article for abutment against a user's body, said article comprising:
   a first absorbent body that has a longitudinal direction, a width direction perpendicular to the longitudinal direction, and a thickness direction perpendicular to both the longitudinal and width directions, the first absorbent body having a body-facing side and a garment-facing side;
   a second absorbent body positionable farther from the user's body than the first absorbent body, the second absorbent body having a body-facing side and a garment-facing side;
   an undetachably joined section in which the garment-facing side of one end section of the first absorbent body in the longitudinal direction with the body-facing side of the second absorbent body are undetachably, permanently joined to each other;
   a detachably joined section in which the garment-facing side of the other end section of the first absorbent body in the longitudinal direction with the body-facing side of the second absorbent body are detachably, temporarily joined to each other; and
   a non-joined section in which the first absorbent body and the second body are not joined to each other;
   wherein the detachably joined section is between the undetachably joined section and the non-joined section.

2. The absorbent article according to claim 1, wherein the non-joined section is a handle section for being held by a user when detaching the first absorbent body and the second absorbent body from each other.

3. A method of producing an absorbent article for abutment against a user's body, said method comprising:
   a continuous-body production step that produces a continuous body in which first absorbent bodies for absorbing fluid are continuously arranged, each said first absorbent body having a longitudinal direction, a width direction perpendicular to the longitudinal direction, and a thickness direction perpendicular to both the longitudinal and width directions, each said first absorbent body having a body-facing side and a garment-facing side; and
   a continuous-body joining step that
      undetachably, permanently joins, at an undetachably joined section, the garment-facing side of one end section of each said first absorbent body in the longitudinal direction with a body-facing side of a second absorbent body,
      detachably, temporarily joins, at a detachably joined section, the garment-facing side of the other end section of each said first absorbent body in the longitudinal direction with the body-facing side of the corresponding second absorbent body, and
      defines a non-joined section in which each said first absorbent body and the corresponding second absorbent body are not joined to each other, wherein the detachably joined section is between the undetachably joined section and the non-joined section.

4. The method according to claim 3, wherein, in the continuous-body joining step, the one end section of each said first absorbent body in the longitudinal direction and the corresponding second absorbent body are undetachably, permanently joined to each other by compression-bonding via an adhesive disposed between the one end section of the first absorbent body and the corresponding second absorbent body.

5. The method according to claim 4, wherein, in the continuous-body joining step, the other end section of each said first absorbent body in the longitudinal direction and the corresponding second absorbent body are detachably, temporarily joined to each other by said compression-bonding without adhesive disposed between the other end section of the first absorbent body and the corresponding second absorbent body.

6. The method according to claim 3, further comprising:
   a reinforced section formation step that forms reinforced sections respectively at the one end section and the other end section of each said first absorbent body in the longitudinal direction by reinforcing the one end section and the other end section,
   wherein
   the reinforced section formed at the other end section is detachably, temporarily joined to the corresponding second absorbent body in the continuous-body joining step, and the reinforced section formed at the one end section is undetachably, permanently joined to the corresponding second absorbent body in the continuous-body joining step.

7. A method of producing an absorbent article for abutment against a user's body, said method comprising:
a single-absorbent-body production step that produces, as a discrete member, a first absorbent body for absorbing fluid, said first absorbent body having a longitudinal direction, a width direction perpendicular to the longitudinal direction, and a thickness direction perpendicular to both the longitudinal and width directions, said first absorbent body having a body-facing side and a garment-facing side; and
an absorbent-body joining step that
undetachably, permanently joins, at an undetachably joined section, the garment-facing side of one end section of said first absorbent body in the longitudinal direction with a body-facing side of a second absorbent body,
detachably, temporarily joins, at a detachably joined section, the garment-facing side of the other end section of said first absorbent body in the longitudinal direction with the body-facing side of the second absorbent body, and
defines a non-joined section in which said first absorbent body and the second absorbent body are not joined to each other, wherein the detachably joined section is between the undetachably joined section and the non-joined section.

8. The method according to claim 7, wherein, in the absorbent-body joining step, the one end section of the first absorbent body in the longitudinal direction and the second absorbent body are undetachably, permanently joined to each other by compression-bonding via an adhesive disposed between the one end section of the first absorbent body and the second absorbent body.

9. The method according to claim 8, wherein, in the absorbent-body joining step, the other end section of the first absorbent body in the longitudinal direction and the second absorbent body are detachably, temporarily joined to each other by compression-bonding without adhesive disposed between the other end section of the first absorbent body and the second absorbent body.

10. The method according to claim 7, further comprising:
a reinforced section formation step that forms reinforced sections respectively at the one end section and the other end section of the first absorbent body in the longitudinal direction by reinforcing the one end section and the other end section,
wherein
the reinforced section formed at the other end section is detachably, temporarily joined to the second absorbent body in the absorbent-body joining step, and
the reinforced section formed at the one end section is undetachably, permanently joined to the second absorbent body in the absorbent-body joining step.

* * * * *